US008138326B2

(12) United States Patent
Gyllensten et al.

(10) Patent No.: US 8,138,326 B2
(45) Date of Patent: Mar. 20, 2012

(54) METHOD AND KIT FOR QUANTITATIVE AND QUALITATIVE DETERMINATION OF HUMAN PAPILLOMAVIRUS

(75) Inventors: Ulf Gyllensten, Uppsala (SE); Martin Moberg, Uppsala (SE)

(73) Assignee: Cepheid Corporation, Sunnyvale, CA (US)

( * ) Notice: Subject to any disclaimer, the term of this patent is extended or adjusted under 35 U.S.C. 154(b) by 1299 days.

(21) Appl. No.: 10/529,447

(22) PCT Filed: Oct. 1, 2003

(86) PCT No.: PCT/SE03/01529
§ 371 (c)(1),
(2), (4) Date: Dec. 12, 2005

(87) PCT Pub. No.: WO2004/031416
PCT Pub. Date: Apr. 15, 2004

(65) Prior Publication Data
US 2007/0037137 A1    Feb. 15, 2007

(30) Foreign Application Priority Data

Oct. 1, 2002    (SE) ..................................... 0202897

(51) Int. Cl.
*C07H 21/04*    (2006.01)
(52) U.S. Cl. ..................................................... 536/24.3
(58) Field of Classification Search .................... None
See application file for complete search history.

(56) References Cited

U.S. PATENT DOCUMENTS

| | | | |
|---|---|---|---|
| 6,228,368 B1 * | 5/2001 | Gissmann et al. | 424/204.1 |
| 6,420,106 B1 | 7/2002 | Gyllensten et al. | |
| 2002/0137021 A1 * | 9/2002 | Kroeger et al. | 435/5 |

OTHER PUBLICATIONS

Marich et al. Human papillomavirus type 35 complete genome. GenBank Accession No. M74117 (2002).*
Marich et al. The phylogenetic relationship and complete nucleotide sequence of human papillomavirus type 35. Virology (1992) 186:770-776.*
Yoo et al. Homo sapiens hydroxymethybilane synthase gene, complete cds. GenBank Accession No. M95623 (1995).*
Yoo et al. Hydroxymethybilane synthase: complete genomic sequence and amplifiable polymorphisms in the human gene. Genomics (1993) 15:21-29.*
Buck et al. Design strategies and performance of custom DNA sequencing primers. BioTechniques (1999) 27:528-536.*
Goldsborough et al. Nucleotide sequence of human papillomavirus type 31: a cervical neoplasia-associated virus. GenBank Accession No. J04353 (1994).*
Seedorf et al. Identification of early proteins of the human papilloma viruses type 16 (HPV 16) and type 18 (HPV18) in cervical carcinoma cells. EMBO J. (1987) 6:139-144.*
Sastre-Garau et al. Distinct patterns of alteration of myc genes associated with integration of human papillomavirus type 16 or type 45 DNA in two genital tumours. J. Gen. Virol. (2000) 81:1983-1993.*
Sastre-Garau et al. Distinct patterns of alteration of myc genes associated with integration of human papillomavirus type 16 or type 45 DNA in two genital tumours. GenBank Accession No. AJ242956 (2006).*
Agnetha M. Josefsson et al, "Viral load of human papilloma virus 16 as a determinant for development of cervical carcinoma in situ: a nested case-control study", *The Lancet*, vol. 355, Jun. 24, 2000, pp. 2189-2193.
Agnetha Josefsson et al, "Detection and Quantitation of Human Papillomavirus by Using the Fluorescent 5' Exonuclease Assay", *Journal of Clinical Microbiology*, vol. 37, No. 3, Mar. 1999, pp. 490-496.
David C. Swan et al, "Human Papillomavirus (HPV) DNA Copy Number Is Dependent on Grade of Cervical Disease and HPV Type", *Journal of Clinical Microbiology*, Apr. 1999, vol. 37, No. 4, pp. 1030-1034.
Nathalie Ylitalo et al, "Detection of Genital Human Papillomavirus by Single-Tube Nested PCR and Type-Specific Oligonucleotide Hybridization", *Journal of Clinical Microbiology*, vol. 33, No. 7, Jul. 1995, pp. 1822-1828.
Nathalie Ylitalo et al, "Consistent high viral load of human papillomavirus 16 and risk of cervical carcinoma in situ: a nested case-control study", *The Lancet*, vol. 355, Jun. 24, 2000, pp. 2194-2198.
Kenneth Livak et al, "Towards fully automated genome-wide polymorphism screening", Nature Genetics, vol. 9, Apr. 1995, pp. 341-342.
Attila T. Lorincz et al, "Viral load of human papillomavirus and risk of CIN3 or cervical cancer", *The Lancet*, vol. 360, Jul. 20, 2002, pp. 228-229.
Martin Moberg et al, "Real-Time PCR-Based System for Simultaneous Quantification of Human Papillomavirus Types Associated with High Risk of Cervical Cancer", *Journal of Clinical Microbiology*, vol. 41, No. 7, Jul. 2003, pp. 3221-3228.
David R. Scott et al, "Use of Human Papillomavirus DNA Testing to Compare Equivocal Cervical Cytologic Interpretations in the United States, Scandinavia, and the United Kingdom", *Cancer Cytopathology*, pp. 14-20, 2002 American Cancer Society.
C.A. Sun et al, "Viral load of high-risk human papillomavirus in cervical squamous intraepithelial lesions", *International Journal of Gynecology& Obstetrics*, 76, 2002, pp. 41-47.
Mark van Duin et al, "Human Papillomavirus 16 Load in Normal and Abnormal Cervical Scrapes: An Indicator of CIN II/III and Viral Clearance", Int. J. Cancer, 98, 590-595 (2002).
Thomas C. Wright, Jr, MD, et al, "2001 Consensus Guidelines for the Management of Women with Cervical Cytological Abnormalities", *JAMA*, Apr. 24, 2002, vol. 287, No. 16, pp. 2120-2129.
Susanne K. Kjaer et al, "Type specific persistence of high risk human papillomavirus (HPV) as indicator of high grade cervical squamous intraepithelial lesions in young women: population based prospective follow up study", *BMJ*, vol. 325, Sep. 14, 2002, pp. 1-7.
D.Y. Chang et al, "Prevalence of single and multiple infection with human papillomaviruses in various grades of cervical neoplasia", *Journal of Medical Microbiology*, vol. 46, 1997, pp. 54-60.

(Continued)

*Primary Examiner* — Kenneth R. Horlick
*Assistant Examiner* — David Thomas
(74) *Attorney, Agent, or Firm* — Poter Wright Morris & Arthur

(57) ABSTRACT

The present invention relates to a method and kit for quantitative and qualitative determination of human papillomavirus, HPV, in a sample. More precisely, for quantitative and qualitative determination of oncogenic HPV to predict the risk of HPV infection resulting in cervical carcinoma. The method and kit enable simultaneous measurement of several oncogenic HPV types.

15 Claims, 11 Drawing Sheets

OTHER PUBLICATIONS

Figure 1:
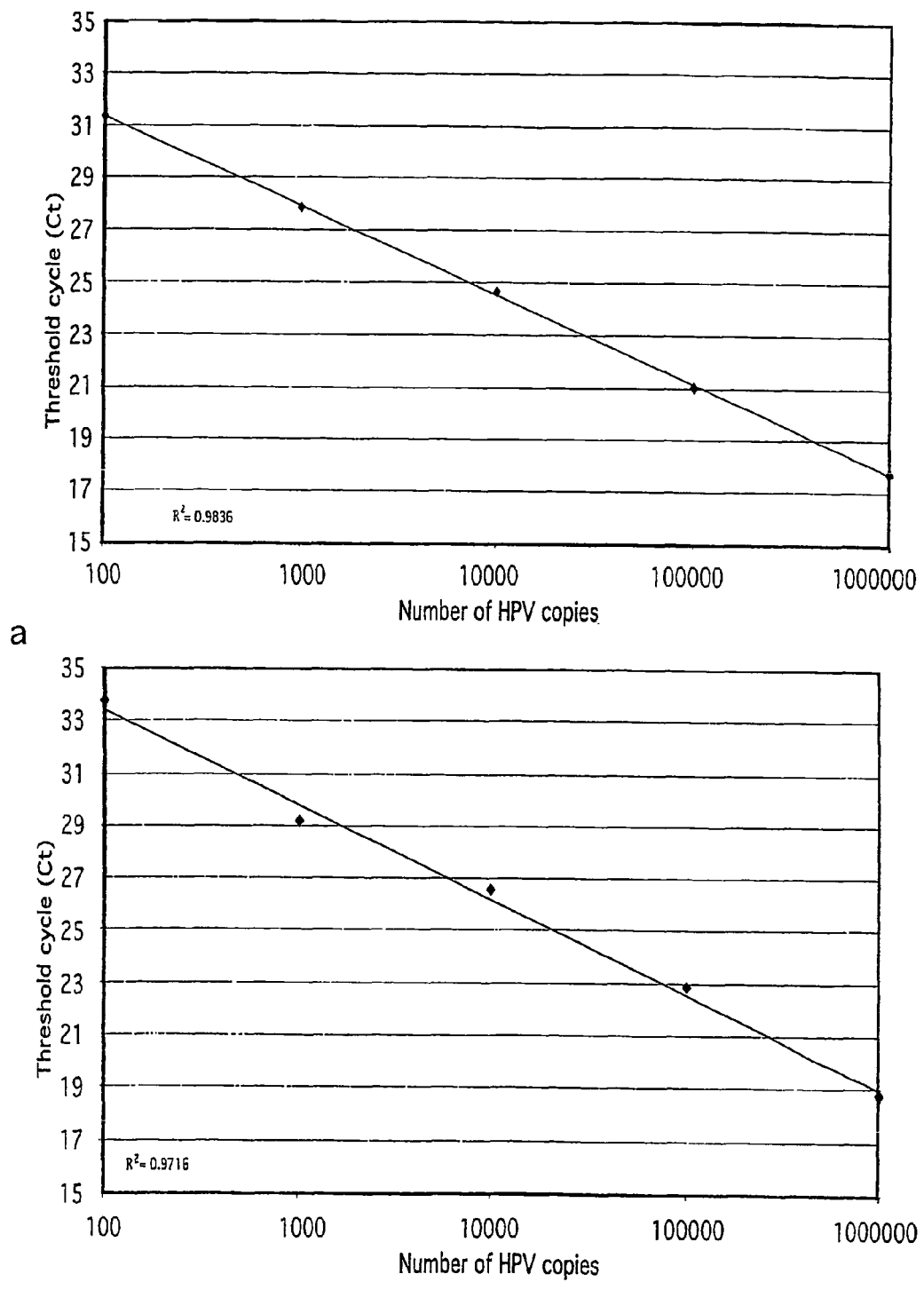

Toshiyuki Sasagawa et al, "High-Risk and Multiple Human Papillomavirus Infections Associated with Cervical Abnormalities in Japanese Women", *Cancer Epidemiology, Biomarkers & Prevention*, vol. 10, Jan. 2001, pp. 45-52.

Ruth Ann Tucker et al, "Real-time PCR-based Fluorescent Assay for Quantitation of Human Papillomavirus Types 6, 11, 16, and 18", *Molecular Diagnosis*, vol. 6, No. 1, 2001, pp. 39-47.

David C. Swan et al, "A Sensitive, Type-Specific, Fluorogenic Probe Assay for Detection of Human Papillomvarisu DNA", *Journal of Clinical Microbiology*, vol. 35, No. 4, Apr. 1997, pp. 886-891.

Steven M. Anderson, "Human Papillomavirus and Cervical Cancer," *Clinical Microbiology Newsletter*, 24(13):113-118 (2002).

* cited by examiner

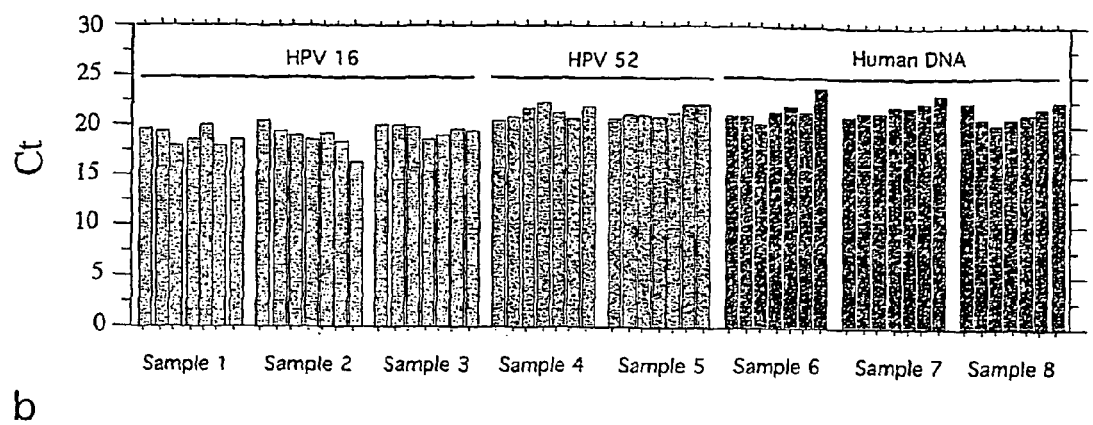
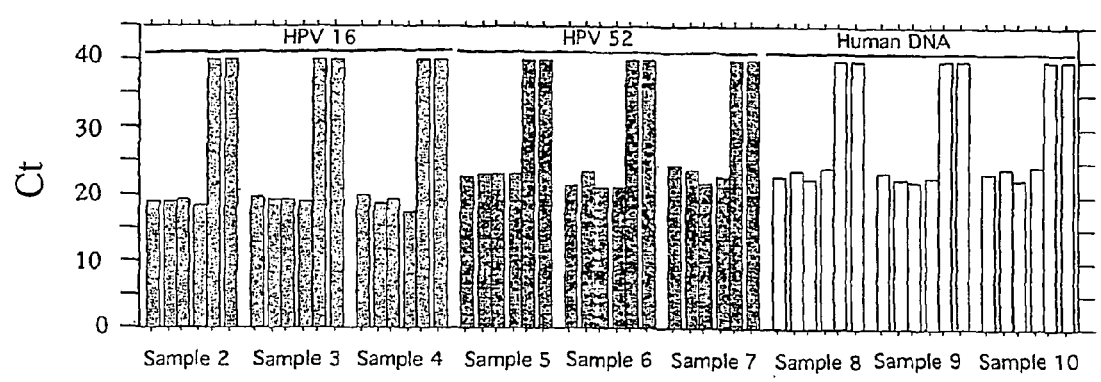
Fig. 7b, c

SEQUENCE LISTING

<160> NUMBER OF SEQ ID NOS: 30

<210> SEQ ID NO 1
<211> LENGTH: 21
<212> TYPE: DNA
<213> ORGANISM: Human papillomavirus type 16

<400> SEQUENCE: 1
agctcagagg aggaggatga a                                          21

<210> SEQ ID NO 2
<211> LENGTH: 23
<212> TYPE: DNA
<213> ORGANISM: Human papillomavirus type 16

<400> SEQUENCE: 2
ggttacaata ttgtaatggg ctc                                        23

<210> SEQ ID NO 3
<211> LENGTH: 22
<212> TYPE: DNA
<213> ORGANISM: Human papillomavirus type 31

<400> SEQUENCE: 3
acgattccac aacataggag ga                                         22

<210> SEQ ID NO 4
<211> LENGTH: 24
<212> TYPE: DNA
<213> ORGANISM: Human papillomavirus type 31

<400> SEQUENCE: 4
tacacttggg tttcagtacg aggt                                       24

<210> SEQ ID NO 5
<211> LENGTH: 21
<212> TYPE: DNA
<213> ORGANISM: Human papillomavirus type 18

<400> SEQUENCE: 5
cattttgtga acaggcagag c                                          21

<210> SEQ ID NO 6
<211> LENGTH: 21
<212> TYPE: DNA
<213> ORGANISM: Human papillomavirus type 45

<400> SEQUENCE: 6
cattttgtga acaggcagag c                                          21

<210> SEQ ID NO 7
<211> LENGTH: 21
<212> TYPE: DNA
<213> ORGANISM: Human papillomavirus type 18

<400> SEQUENCE: 7
acttgtgcat cattgtggac c                                          21

<210> SEQ ID NO 8
<211> LENGTH: 22
<212> TYPE: DNA
<213> ORGANISM: Human papillomavirus type 45

```
<400> SEQUENCE: 8
caacacctgt gcatcattct ga                                          22

<210> SEQ ID NO 9
<211> LENGTH: 18
<212> TYPE: DNA
<213> ORGANISM: Human papillomavirus type 35

<400> SEQUENCE: 9
accaaagcct gctccgtg                                               18

<210> SEQ ID NO 10
<211> LENGTH: 18
<212> TYPE: DNA
<213> ORGANISM: Human papillomavirus type 35

<400> SEQUENCE: 10
agtcgcactc gcttggtg                                               18

<210> SEQ ID NO 11
<211> LENGTH: 24
<212> TYPE: DNA
<213> ORGANISM: Human papillomavirus type 39

<400> SEQUENCE: 11
cgagcaatta ggagagtcag agga                                        24

<210> SEQ ID NO 12
<211> LENGTH: 20
<212> TYPE: DNA
<213> ORGANISM: Human papillomavirus type 39

<400> SEQUENCE: 12
ctgtggttca tcccgtctgg                                             20

<210> SEQ ID NO 13
<211> LENGTH: 18
<212> TYPE: DNA
<213> ORGANISM: Human papillomavirus type 33

<400> SEQUENCE: 13
cgtcgcaggc gtaaacgt                                               18

<210> SEQ ID NO 14
<211> LENGTH: 18
<212> TYPE: DNA
<213> ORGANISM: Human papillomavirus type 52

<400> SEQUENCE: 14
cgtcgcaggc gtaaacgt                                               18

<210> SEQ ID NO 15
<211> LENGTH: 22
<212> TYPE: DNA
<213> ORGANISM: Human papillomavirus type 33

<400> SEQUENCE: 15
acaggaggca ggtacactgt gg                                          22

<210> SEQ ID NO 16
<211> LENGTH: 20
<212> TYPE: DNA
<213> ORGANISM: Human papillomavirus type 58
```

```
<400> SEQUENCE: 16
tgcgtcgcag acgtaaacgt                                              20

<210> SEQ ID NO 17
<211> LENGTH: 22
<212> TYPE: DNA
<213> ORGANISM: Human papillomavirus type 52

<400> SEQUENCE: 17
acaggaggca ggtacacagt gg                                           22

<210> SEQ ID NO 18
<211> LENGTH: 22
<212> TYPE: DNA
<213> ORGANISM: Human papillomavirus type 58

<400> SEQUENCE: 18
acaggaggca ggtacacagt gg                                           22

<210> SEQ ID NO 19
<211> LENGTH: 21
<212> TYPE: DNA
<213> ORGANISM: Homo sapiens

<400> SEQUENCE: 19
gcctgcagtt tgaaatcagt g                                            21

<210> SEQ ID NO 20
<211> LENGTH: 19
<212> TYPE: DNA
<213> ORGANISM: Homo sapiens

<400> SEQUENCE: 20
cgggacgggc tttagctat                                               19

<210> SEQ ID NO 21
<211> LENGTH: 22
<212> TYPE: DNA
<213> ORGANISM: Human papillomavirus type 16

<400> SEQUENCE: 21
ccagctggac aagcagaacc gg                                           22

<210> SEQ ID NO 22
<211> LENGTH: 23
<212> TYPE: DNA
<213> ORGANISM: Human papillomavirus type 31

<400> SEQUENCE: 22
ctccaacatg ctatgcaacg tcc                                          23

<210> SEQ ID NO 23
<211> LENGTH: 26
<212> TYPE: DNA
<213> ORGANISM: Human papillomavirus type 18

<400> SEQUENCE: 23
agagacagca caggcattgt tccatg                                       26

<210> SEQ ID NO 24
<211> LENGTH: 26
<212> TYPE: DNA
<213> ORGANISM: Human papillomavirus type 45
```

-continued

```
<400> SEQUENCE: 24
agagacagca caggcattgt tccatg                                          26

<210> SEQ ID NO 25
<211> LENGTH: 30
<212> TYPE: DNA
<213> ORGANISM: Human papillomavirus type 35

<400> SEQUENCE: 25
cagaagacaa atcacaaacg acttcgaggg                                      30

<210> SEQ ID NO 26
<211> LENGTH: 27
<212> TYPE: DNA
<213> ORGANISM: Human papillomavirus type 39

<400> SEQUENCE: 26
aacccgacca tgcagttaat caccaac                                         27

<210> SEQ ID NO 27
<211> LENGTH: 22
<212> TYPE: DNA
<213> ORGANISM: Human papillomavirus type 33

<400> SEQUENCE: 27
agatgtccgt gtggcggcct ag                                              22

<210> SEQ ID NO 28
<211> LENGTH: 22
<212> TYPE: DNA
<213> ORGANISM: Human papillomavirus type 52

<400> SEQUENCE: 28
agatgtccgt gtggcggcct ag                                              22

<210> SEQ ID NO 29
<211> LENGTH: 22
<212> TYPE: DNA
<213> ORGANISM: Human papillomavirus type 58

<400> SEQUENCE: 29
agatgtccgt gtggcggcct ag                                              22

<210> SEQ ID NO 30
<211> LENGTH: 26
<212> TYPE: DNA
<213> ORGANISM: Homo sapiens

<400> SEQUENCE: 30
tggaagctaa tgggaagccc agtacc                                          26
```

METHOD AND KIT FOR QUANTITATIVE AND QUALITATIVE DETERMINATION OF HUMAN PAPILLOMAVIRUS

RELATED APPLICATION

This application is a 371 of PCT/SE2003/001529.

FIELD OF THE INVENTION

The present invention relates to a method and kit for quantitative and qualitative determination of human papillomavirus, HPV, in a sample. More precisely, for quantitative and qualitative determination of oncogenic HPV to predict the risk of HPV infection resulting in cervical carcinoma.

BACKGROUND OF THE INVENTION

Cervical carcinoma is considered to be the third most common cancer in women in the world. In 1994 an estimated 55.000 women in the U.S. were diagnosed with carcinoma in situ of the cervix, with an additional 15.000 cases of invasive cancer. Although organized or voluntary screening is available in a number of countries and a range of interventions exist, about 4.600 of women diagnosed with the disease do not survive. In Sweden organized screening has been in operation for the last 20 years, but still about 500 cases of invasive cancer are diagnosed annually. Although in the US and Europe major progress has been made in the control of cervical cancer, it remains a significant cause of morbidity and mortality in the developing world.

Infection by certain types of human papillomavirus (HPV) is the single most important risk factor for the development of cervical cancer. More than 95% of cervical cancer biopsies have been found to contain DNA of high-risk HPV types, most commonly HPV 16, followed by HPV 18, 45, 31 and 33. Given the importance of HPV infection in the etiology of cervical cancer, a large number of methods have been developed for detecting of the virus or for identifying the cellular changes resulting from viral transformation. Serological detection methods have been used to detect present or recent infection with HPV, but have a limitation in that not every infected individual develop antibodies. A number of DNA technologies have been employed for detection of viral nucleic acid, such as in situ hybridization, restriction fragment length polymorphism (RFLP) and southern-blot analysis, hybrid capture (where a DNA-RNA heteroduplex is recognized by monoclonal antibodies) and various PCR based assays. Many of the PCR systems developed for HPV detection involve an amplification step followed by a separate step for identification of individual HPV types To increase the technical sensitivity of the assay when analyzing samples with limited DNA, such as formalin-fixed biopsies or archival Papanicolaou (Pap) cervical smears, a nested-PCR has frequently been employed.

Previously an assay based on real-time PCR for the detection and quantification of high risk HPV DNA has been described (Josefsson et al., 1999). The 5' exonuclease assay, employed in real-time PCR, is based on the ability of the 5' to 3' exonuclease activity of Taq polymerase to cleave a dual-labeled, non-extendible, hybridization probe during the extension phase of the PCR.

Using this previously described method it was demonstrated, in a case-control study, that the titer of HPV 16 in cervical smears can be used to predict the risk of development of cervical cancer in situ (cervical interstitial neoplasia, stage II; CIN III) (Josefsson et al., 2000; Ylitalo et al., 2000). These results indicate that HPV titer may represent a powerful means of determining whether an infection will progress into cervical cancer or be cleared. This invention is described in U.S. Pat. No. 6,420,106 and relates to a method to predict the risk of progression to virus associated cancer in a human subject.

SUMMARY OF THE INVENTION

The present invention relates to a method and kit for quantitative as well as qualitative determination of human papillomavirus. The method of the invention gives a quantitative and qualitative measure as a basis of the predicted outcome of an HPV infection. The method and kit of the invention have a wide coverage of oncogenic HPV types without being complex and time consuming. The invention relates to an assay and kit for simultaneous measurement of several HPV types, employing the quantitative ability and dynamic range provided by real-time PCR. The invention has the advantage of detecting and quantifying the HPV types most commonly detected in cervical tumors, while minimizing the number of parallel reactions performed for each sample, making the system suitable for use in routine screening of cervical swab samples. According to one embodiment of the invention, an optimized test system enables sample determination in two tests and a separate test for normalization.

Thus, in a first aspect the invention relates to a method for quantitative and qualitative determination of human papillomavirus (HPV) in a sample comprising the steps of:
i) providing a sample from a patient suspected to be infected by HPV, and optionally extracting the nucleic acid of the sample,
ii) dividing the sample or nucleic acid from the sample in two or more sub-samples or equal aliquots,
iii) measuring, simultaneously, the presence and amount of two or more viruses in one of said sub-samples by using a specific primer for amplification of each virus or group of viruses, whereby the primers are designed not to compete during the amplification-reaction, and a specific probe for each virus or group of viruses, whereby the probes are designed not to compete during the amplification-reaction and the detection phase,
iv) determining the amount of said sample by analysis of a nuclear gene in a given amount of another of said sub-samples in a separate amplification reaction
v) calculating the amount of each virus or group of viruses per amount of sample from the results of steps iii) and iv).

Preferably the amplifications in steps iii) and iv) are PCR amplifications and more preferably the method is a PCR-based fluorescent 5' exonuclease assay.

The viruses in step iii) are chosen from HPV 16, 18, 31, 33, 35, 39, 45, 51, 52, 56, 58, 59, 67 and 68.

According to a preferred embodiment HPV 16, 18, 31, 45 is detected and quantified in one sub-sample and optionally HPV 33, 35, 39, 52, 58 and 67 is detected and quantified in another sub-sample. In an initial series of experiments HPV 67 was detected and measured but according to an at present preferred embodiment of the invention HPV 67 is not included in the kit and the method using the kit.

Preferably, the amount of a human single copy gene is detected and quantified in step iv). This gene may be HUMPBGDA, Homo sapiens hydroxymethylbilane synthase gene, accnr M95623.1.

The method of the invention is preferably used for detection and diagnose of cervical cancer.

In a second aspect, the invention relates to a kit for detection and quantification of human papillomavirus, comprising a) seven amplification primers and three probes for HPV 16, 31, 18, 45 according to Table 1 and 2 of the specification; and optionally
b) eight amplification primers and three probes for HPV 33, 35, 39, 52, and 58, according to Table 1 and 2 of the specification.

Preferably, the kit further comprises two amplification primers and one probe, according to Table 1 and 2 of the specification, for detection and quantification of the amount of a human single copy gene, such as HUMPBGDA, Homo sapiens hydroxymethylbilane synthase gene, accnr M95623.1.

In a preferred embodiment the kit further comprises at least two different fluorophores, In one embodiment the kit comprises
a) seven amplification primers and three probes for HPV 16, 31, 18, 45 according to Table 1 and 2 of the specification;
b) eight amplification primers and three probes for HPV 33, 35, 39, 52, and 58, according to Table 1 and 2 of the specification;
c) two amplification primers and one probe, according to Table 1 and 2 of the specification, for detection and quantification of the amount of a human single copy gene; and
d) three different fluorophores.

The kit of the invention is preferably used for detection and diagnose of cervical cancer. For this purpose, the kit may also optionally comprise a cervical swab.

DETAILED DESCRIPTION OF THE INVENTION

Materials and Methods

DNA Extraction

Plasmids containing HPV 16, 18, 31, 33, 35, 39, 45, 52, 58 and 67 were used as positive controls and to estimate the sensitivity of the assay: The plasmids with integrated HPV were transformed into One Shot cells (INV a,F', Invitrogen TA Cloning kit, Groningen, NL) and positive transformants isolated, grown in 100 ml LB in 37° C. overnight and plasmid DNA extracted using the Qiagen Maxiprep kit (Qiagen, WWR): The copy numbers for individual plasmid preparations were estimated using spectrophotometrical determination of the OD.

DNA from blood samples, used for development of the human nuclear gene assay, was extracted using a standard protocol based on proteinase K treatment, followed by phenol/chloroform extraction and ethanol precipitation. DNA from formalin-fixed biopsies was extracted using published protocols. DNA purity and concentration was determined by optical density measurements (GeneQuant. Pharma Biotech, Cambridge, England).

For studies of the DNA from archival smears a modification of a previously described protol was used. Briefly, this protocol includes incubation in xylen to remove the cover slip, astaining, proteinase K treatment (60° C. minimum 1 hour) and subsequently a transfer of cells to sterile Eppendorf tubes. Saturated ammonium acetate is then added to precipitate the protein. The DNA supernatant is recovered with ethanol, the pellet washed with 70% ethanol, dried and dissolved in 200 µl TE-low (10 mM Tris-HCl, pH 7.4, 0.1 mM EDTA).

Sample Preparation from Cervical Swabs

For the study of extraction protocols we used cervical swab samples and compared five different extraction protocols (A-E).

Protocol A is based on freezing and boiling of the samples. Briefly, the cervical swab (or brush is immersed in 1 ml PBS and swirled to release the cells. 250 µl of this suspension is use in the protocol below. The solution is spun at 3.000 g for 10 min in a tabletop centrifuge. The supernatant is collected and 250 µl, 10 mM Tris-HCl pH 7.4 is added. The sample is then vortexed carefully to distribute the cells evenly. 100 µl of the solution is transferred to a new Eppendorf tube and both the 100 µl aliquot and the remaining volume (used as backup) are frozen at −20° C. The 100 µl aliquot is then thawn and boiled in a heating block at 100° C. for 10 min. The tube is briefly centrifuged to pull down condensed water and 2 µl of the suspension is used for the Taqman reaction.

In protocol B, a commercial kit for DNA extraction based on precipitation of proteins (Wizard, Promega, Madison, Wis., USA) is used. Briefly, the cervical swab (or brush) is immersed in 1 ml PBS and swirled to release the cells. 250 µl of this suspension is used in the protocol below. The solution is spun at max speed in an Eppendorf centrifuge for 5 min. The supernatent is discarded and 300 µl Nuclei Lysis Solution (Wizard kit) is added. The solution is mixed by pipetting and incubated at 37° C. for 1 h. The sample is cooled to RT and 100 µl protein precipitation solution (Wizard kit) is added. The solution is then vortexed for 10-20 sec and centrifuged at 13-16.000 g for 3 min. The supernatant is transferred to a new Eppendorf tube with 300 µl isopropanol (at RT), the solutions mixed and centrifuged at 13-16.000 g for 1 min. The supernatant is removed and the pellet washed with 70% ethanol and centrifuged again at 13-16.000 g for 1 min. Finally, the ethanol is removed and the pellet air dried. The pellet is dissolved in 100 µl of Rehydration solution (10 mM Tris-HCl, 1 mM EDTA, pH 7.4), incubated at 65° C. for 1 h and 2 µl used for each Taqman reaction.

Protocol C is based on proteinase K digestion of the samples. Briefly, the cervical swab (or brush) is immersed in 1 ml PBS and swirled to release the cells. 250 µl of this suspension is used in the protocol below. The solution is spun at max speed in an Eppendorf centrifuge for 5 min. The supernatant is removed and a Proteinase K solution (148 µl digestion buffer (Tris-base 50 mM, 0.5% Tween 20, 1 mM EDTA) and 1.95 µl proteinase K (20 mg/ml) is added. The sample is incubated at 56° C. for 2 hr and the proteinase K inactivated at 95° C. for 5 min. The sample is finally centrifuged for 5 min and 2 µl of the top phase used for each Taqman reaction.

Protocol D includes organic extraction (phenol/chloroform) of the samples. First, protocol B above is used including the addition of the Nuclei Lysis Solution (Wizard kit) and incubation at 37° C. for 1 h. Then 300 µl of equilibrated phenol is added to the sample. The solution is mixed, spun and the water phase extracted once more with phenol, then with chloroform and the DNA is collected by ethanol precipitation, the pellet is washed and dried and dissolved in 100 µl TE low. 2 µl of the dissolved DNA preparation is used for each Taqman reaction.

Finally, in protocol E, a commercial kit for DNA extraction based on binding of nucleic acid to glass beads (Nuclisens, Nasba diagnostics, Organon-Teknica, Boxtel, NL), is used. Lysis buffer and wash buffer is heated to 37° C. for 30 min (vortex every 10 min.). The wash buffer and lysis buffer is subsequently cooled to RT. The sample (10-200 µl of cervical swab solution) is then added to 900 µl Lysis buffer, the mixture is vortexed and the tube spun at 10.000 g for 30 sec. The silica solution is vortexed until it becomes opaque, 50 µl is added to each sample and the mixture vortexed. The tube is incubated at room temperature for 10 min. and vortexed every second minute. The silica beads are spun down at 10.000 g, 30 sec, the supernatant is removed and 1 ml wash buffer added. The pellet is vortexed until dissolved and washed first with 1 ml 70% ethanol (twice), and then with 1 ml acetone (once).

Residual acetone is carefully removed (with a 100 μl pipette) and the pellet is dried at 56° C. for 10 min. When the silica pellet is dry, 50 μl elution buffer is added and the tube vortexed until the pellet is dissolved. The tube is incubated at 56° C. for 10 min, with intermittent vortexing to avoid sedimentation of the silica. The samples are centrifuged for 2 min at 10.000 g and the supernatant (30-35 μl) transferred to a new tube. 2-5 μl for supernatant is used for each Taqman reaction.

Primers

Oligonucleotide primers 15-24 bp were designed using the program Oligo vs 6.6 (Dynal AS, Oslo) and Primer express (ABI, Foster City, Calif., USA).

Probes

The probes were 22-30 bp in length to ensure a higher $T_m$ than for the primers. The probes were synthesized by Applied Biosystems, Cheshire, UK and Cybergene (Huddinge, Sweden), made such to avoid a guanosine at the most 5' end and HPLC purified prior to use.

Real Time PCR

The PCR amplification was performed in a 25 μl volume containing 1× Buffer A (Applied Biosystems, Foster City, Calif., USA), 3.5 mM $MgCl_2$, 200 nM each of dATP, dCTP, dGTP and 400 nM dUTP (Pharmacia Biotech, Uppsala, Sweden), 0.625 U AmpliTaq Gold (Applied Biosystems, Foster City, Calif., USA), 3.1 μg BSA (Sigma) and 200 nM of each primer and probe, and DNA (according to the extraction protocol).

Amplification and detection was performed using a 7700 Sequence Detection System (Applied Biosystems, Inc.). The amplification ramp included an initial hold program of 10 min. at 95° C. to release the activity of the Taq DNA polymerase. The hold step was followed by a two-step cycle consisting of 15 sec. at 95° C. and 1 min. at 57° C. In the development of the assay we used 50 PCR cycles, while in the analysis of clinical samples only 40 cycles were used due to the high efficiency of the PCR. Tubes, including all PCR components, but without template DNA (denoted NTC reactions), were used to ensure that the reagents mix were free of contamination.

Calculations

The Sequence Detection System software (Applied Biosystems, Foster City, Calif., USA) was used to produce a file with raw data. A dedicated software was used for the calculation of threshold cycle number and conversion into HPV copy numbers per cell.

Statistics

Statistics and graphs were produced using Microsoft excel, Statview and SAS.

RESULTS

The results of the invention will be described below in association with the accompanying figures.

FIG. 1. Standard curves for a) the HPV 16 and b) the HPV 31 assays. The threshold cycle (Ct) number is plotted against the log copy number of HPV. The points represent the mean of 12 independent measurements.

Figure 2:
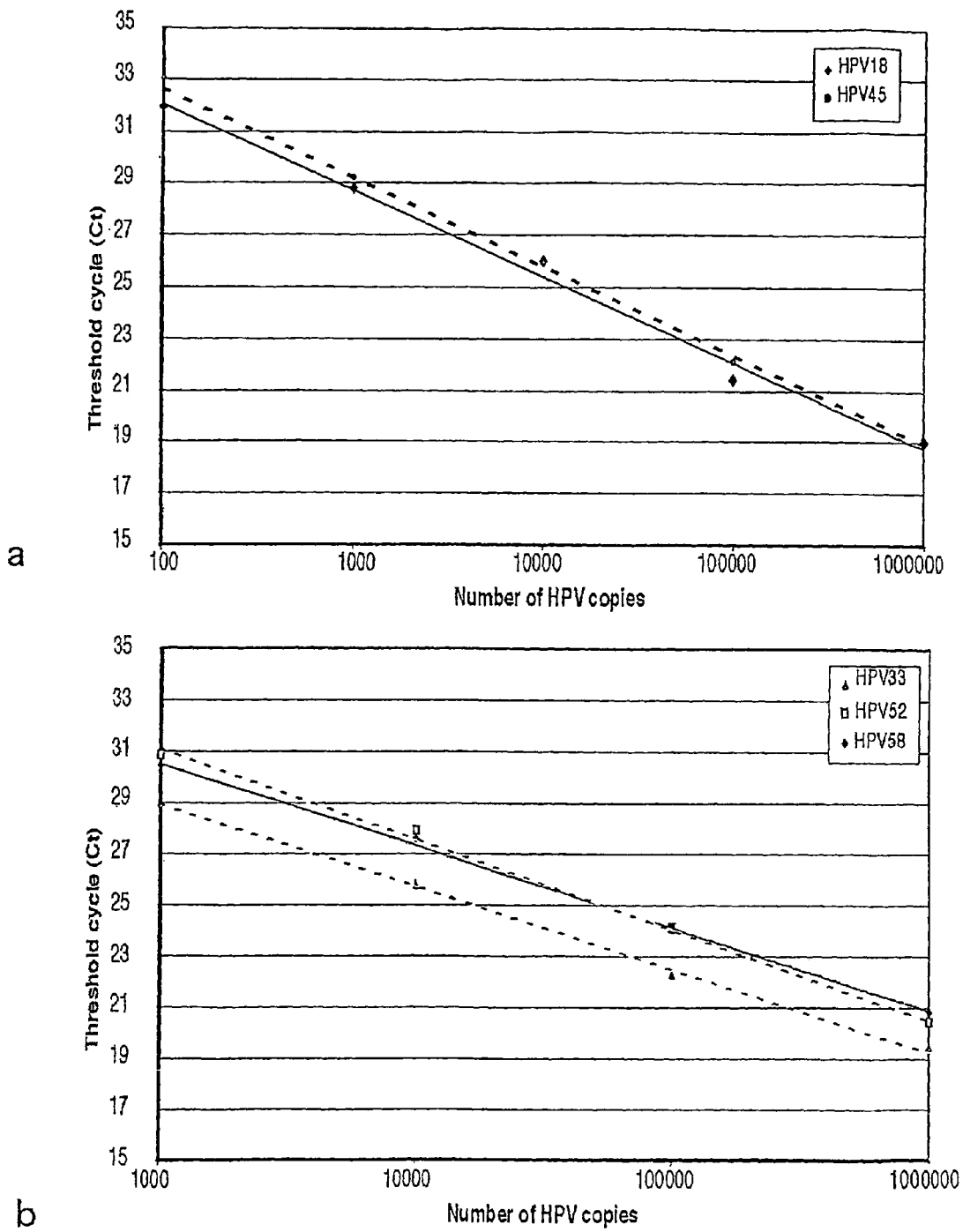

FIG. 2. Standard curves for a) the HPV 18 (solid line) and HPV 45 (dashed line) and b) the HPV 33 group (33, 52, 58) assays. The threshold cycle (Ct) number is plotted against the log copy number of HPV. The points represent the mean of 12 independent measurements.

Figure 3:
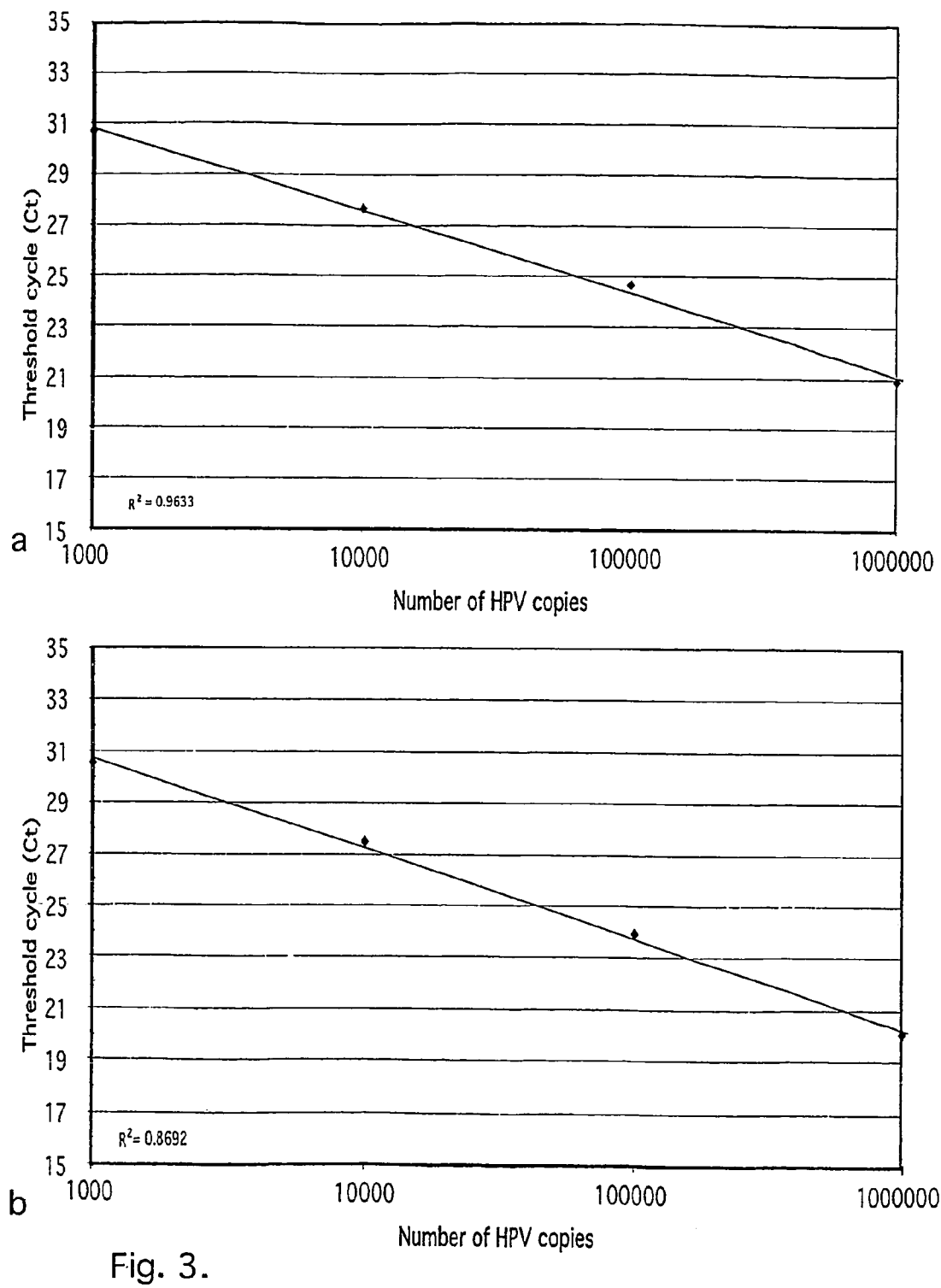

FIG. 3. Standard curves for a) the HPV 35 and b) the HPV 39 assays. The threshold cycle (Ct) number is plotted against the log copy number of HPV. The points represent the mean of 12 independent measurements.

Figure 4:
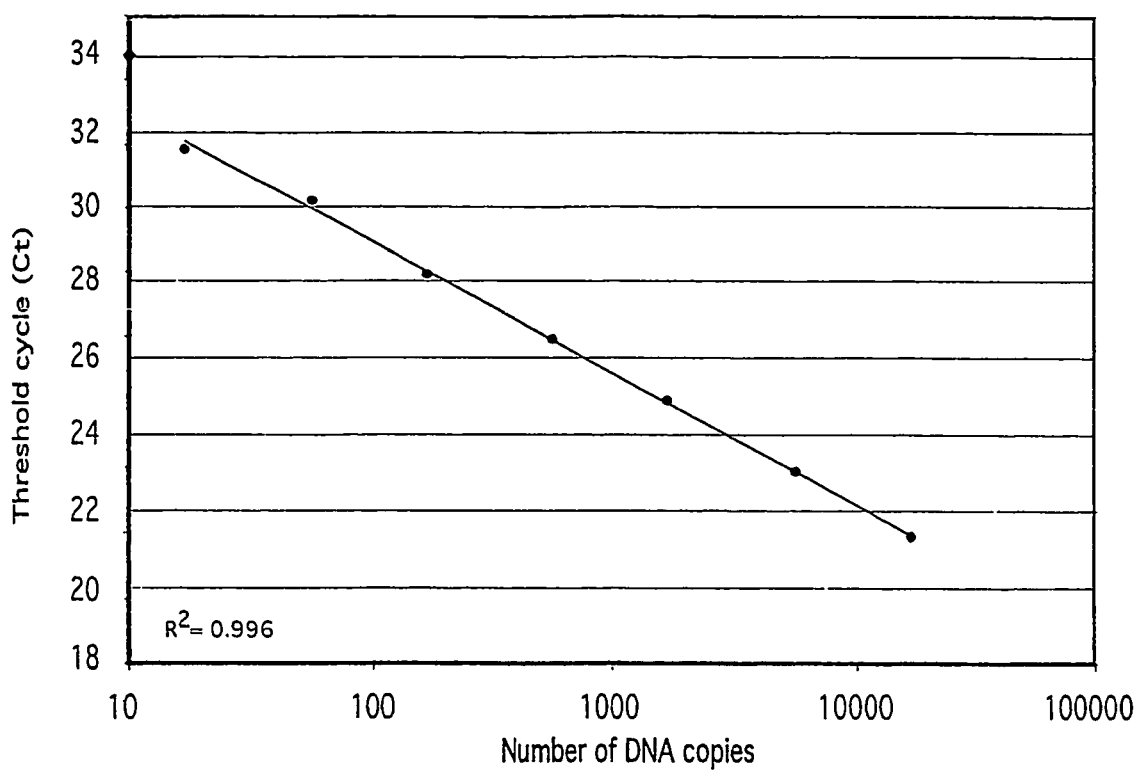

FIG. 4. Standard curves for the human gene (HUMPBGDA) assay. The threshold cycle (Ct) number is plotted against the log copy number of HPV. The points represent the mean of 12 independent measurements.

Figure 5:
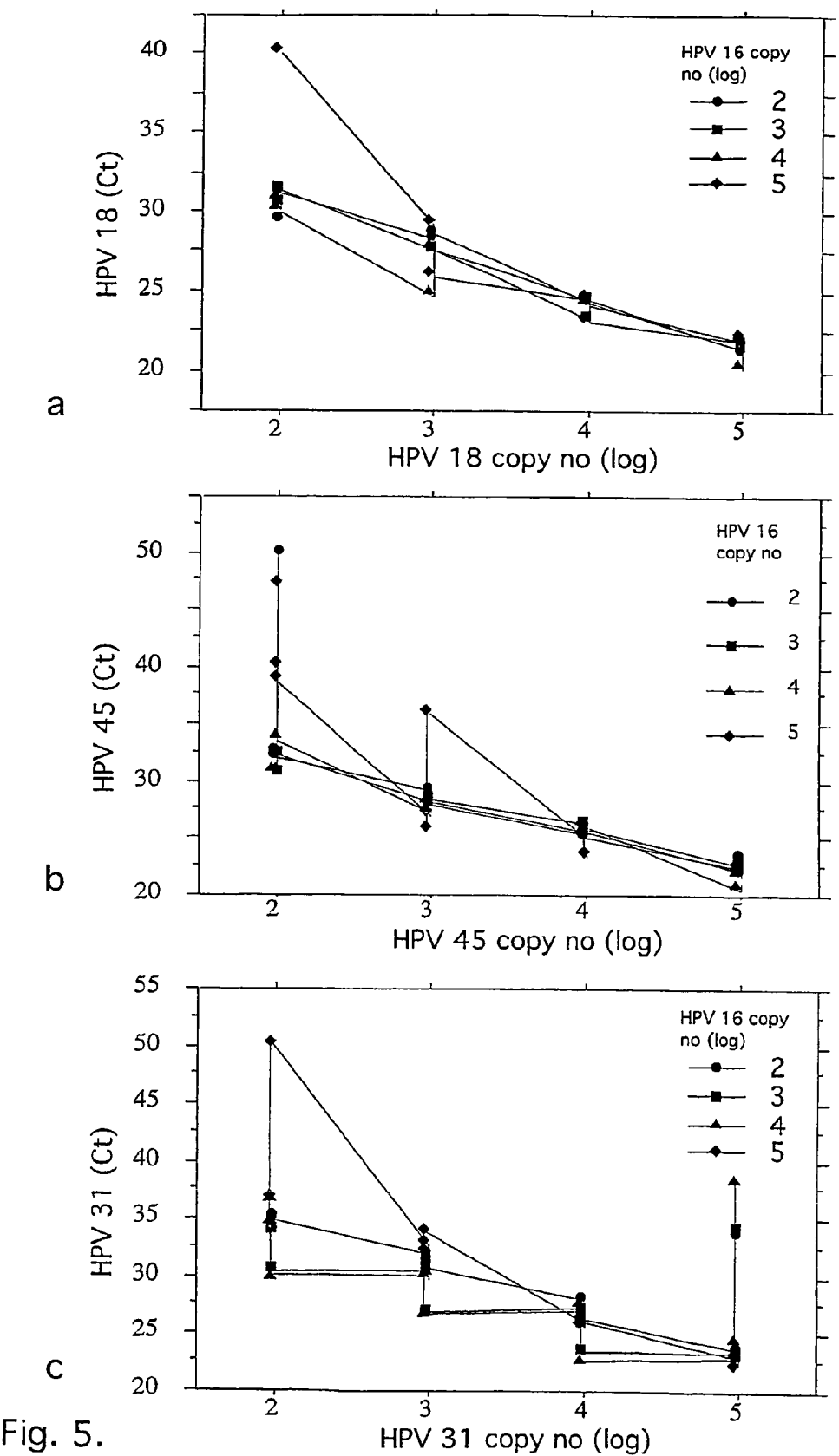

FIG. 5. Analysis of individual HPV types in synthetic mixtures made to mimic mixed infections: a) detection of HPV 18 in a background of HPV 16, b) detection of HPV 45 in a background of HPV 16, c) detection of HPV 31 in a background of HPV 16.

Figure 6:
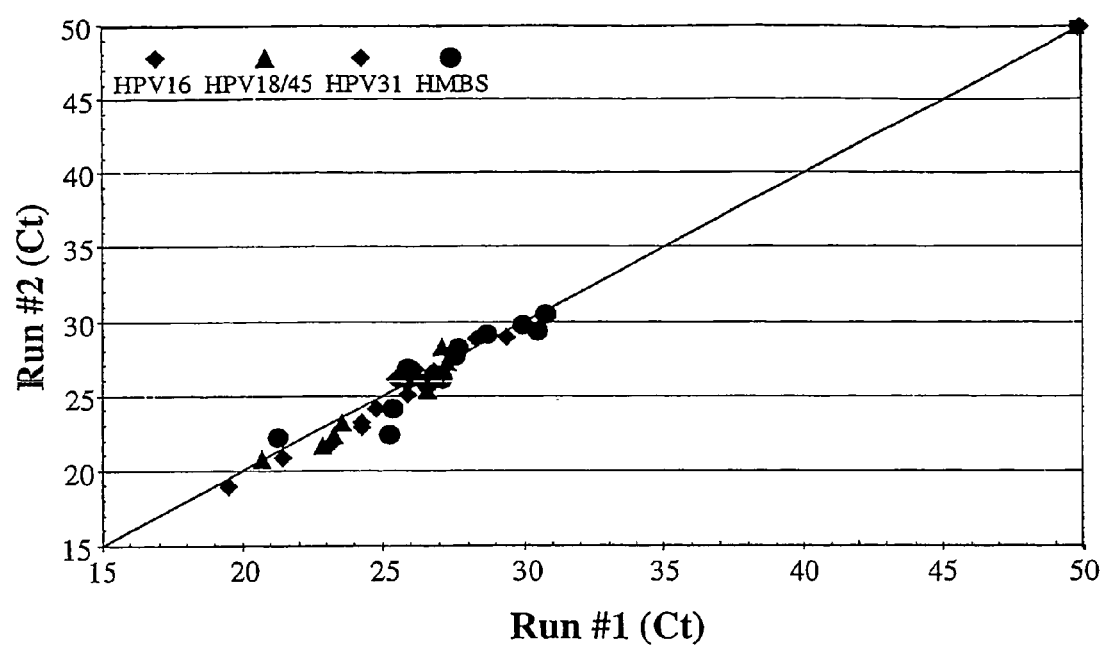

FIG. 6. Comparison of the threshold cycle (Ct) values in two independent runs of the same set of cervical smear samples.

FIG. 7. Stability of the assay reagents at three different storage temperatures: a) −20° C. (4 time-points), b) −4° C., (7 time-points) and c) +30° C. (6 time-points). The bars refer to the Ct values of samples at different time points for individual samples.

Figure 8:
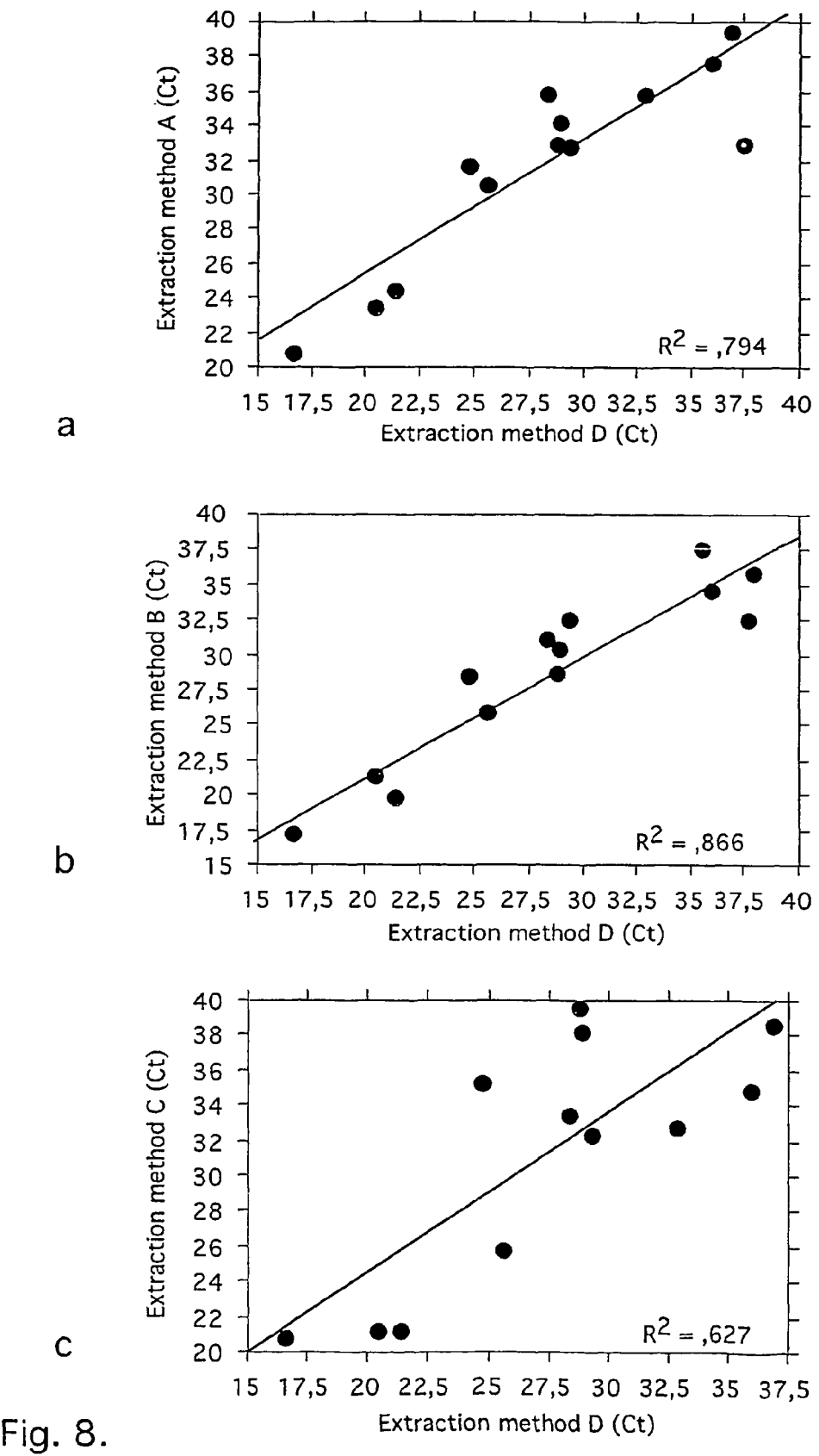
Figure 8:
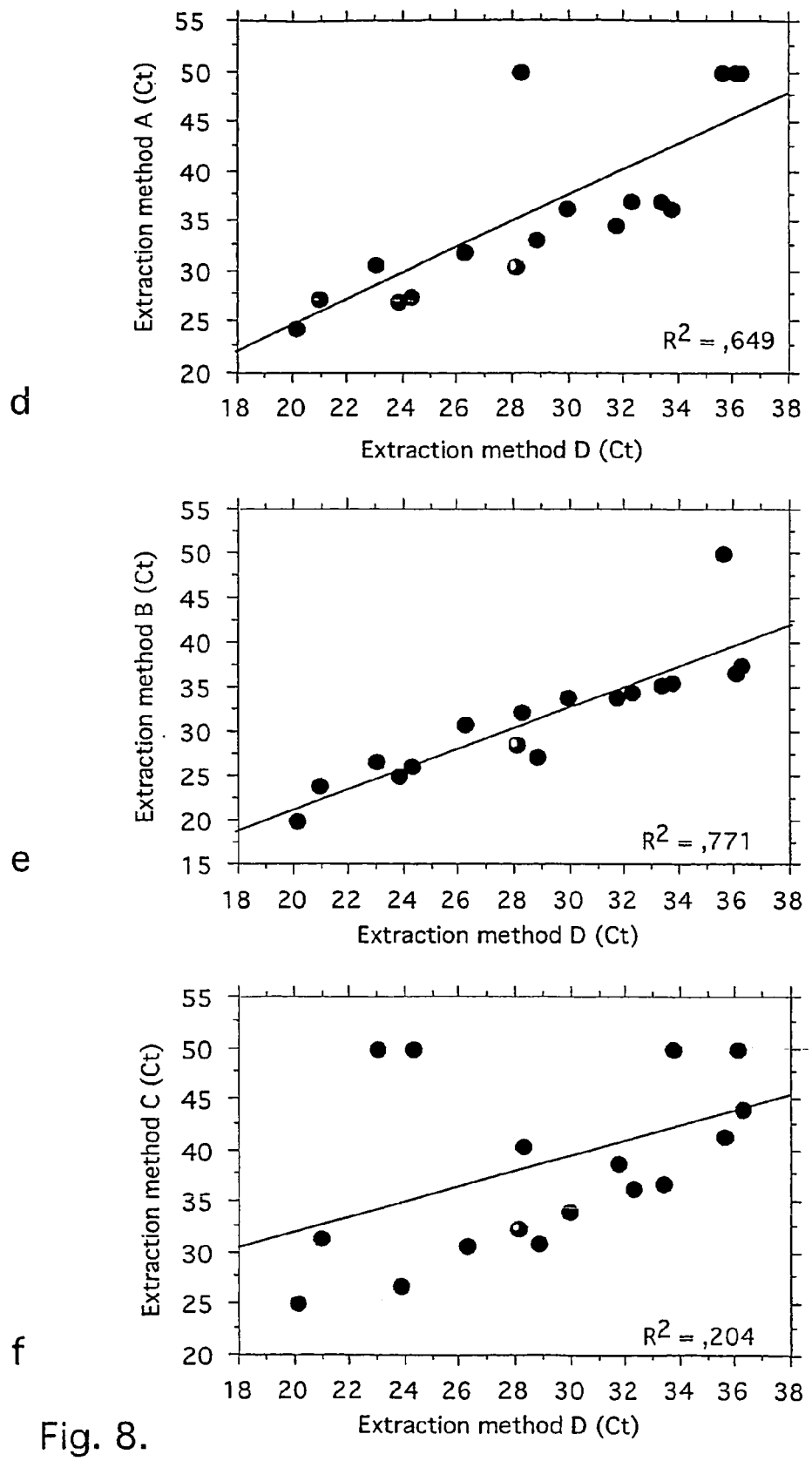

FIG. 8. Comparison of the assay results of using different extraction protocols: a) HPV assay, Protocol A versus Protocol D, b) HPV assay, B vs D, c) HPV assay, C vs D, d) Nuclear gene assay, A vs B, e) Nuclear gene assay, B vs D, f) Nuclear gene assay, C vs D.

Figure 9:
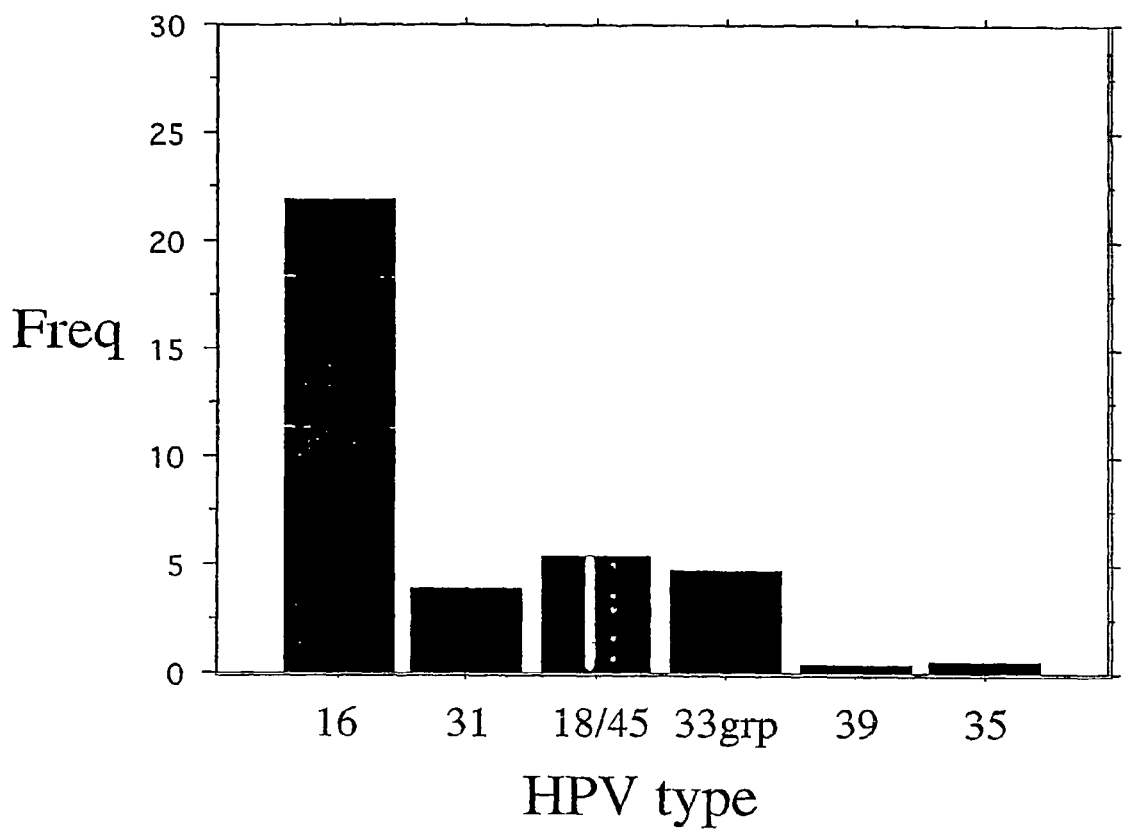

FIG. 9. Frequency distribution of HPV types in a case/control material of cervical smear samples.

RATIONAL AND DESIGN OF THE METHOD AND KIT OF THE INVENTION

The method and kit of the present invention were designed to permit viral load estimates for the range of HPV types most frequently found in different grades of cervical interstitial neoplasia (CIN I-III) and cervical tumors. While the set of HPV types varies between studies, we focused on HPV 16, 18, 31, 33, 35, 39, 45, 52, 58 and 67. The template of the present invention further comprises HPV 51, 56, 59 and 68. These HPV types are found in about 80-90% of cases with cervical cancer in situ and invasive cervical cancer and, thus, the test has the potential to detect 80-90% of women with an oncogenic HPV infection.

The HPV types detected by the assay differ substantially at the nucleotide level, necessitating the use of a series of PCR primers and complicating the development of a typing system capable of detecting a range of HPV types. The real-time PCR method chosen has a very wide dynamic range and excellent characteristics for quantification, but works optimally with the commercially available software only when a single target is assayed and quantified in each reaction. Since our assay was intended for large scale screening purposes and clinical typing, performing a single PCR assay for each HPV type would be sub-optimal. Given these limitations the assay designed is performed in three reaction tubes. The assay is based on three parallel real-time PCRs from each patient sample: a) Reaction 1 detects and quantifies HPV types 16, 31, 18 and 45 (HPV 18 and 45 detected and quantified together) using three different fluorophores, b) Reaction 2 detects and quantifies HPV types 33, 35, 39, 52, 58 and 67 (HPV 33, 52, 58 and 67 detected and quantified together), again using three different fluorophores, and c) Reaction 3 detects and quantifies the amount of a human single copy gene (HUMPBGDA, Homo sapiens hydroxymethylbilane synthase gene, accnr M95623.1). Reaction 1 includes a total of seven PCR primers and three probes, Reaction 2 a total of seven PCR primers and three probes and Reaction 3, two PCR primers and a single probe (Tables 1 and 2).

Primers and probes were designed to optimize the ability for balanced co-amplification of different HPV types in mixed samples. In order to find the most suitable priming sites for co-amplification, and avoid hindrances to an efficient PCR such as regions with strong secondary structure, the amplicons were located in different HPV reading frames. Consequently, in Reaction 1 the amplicon for HPV 16 is located in E7, that for HPV 18/45 in E1 and the amplicon for HPV 31 in E6. The amplicons detected in Reaction 2 are located in L1 (HPV 33, 52, 58, 67), E7 (HPV 39) and E4 (HPV 35). The PCR primers for the human gene span an intron-exon junction (nts:4750-4868).

Technical Sensitivity and Specificity

The sensitivity and specificity of the HPV assay was determined using plasmids containing the entire genome of the different HPV types studied, together with $33 \times 10^{-6}$ g human genomic DNA to mimic the complex nucleic acid environment present in an amplification from genomic DNA (such as cervical smear samples). Plasmid copy numbers were calculated from OD measurements and dilution series were made with $10^2$-$10^7$ HPV copies and high molecular weight human genomic DNA (lacking integrated HPV) was added. Standard curves ranging from $10^2$-$10^7$ copies per sample were constructed for each of the HPV types, or groups of HPV types, based on 12 independent measurements for each HPV copy number (FIG. 1-3). A highly significant linear regression between HPV copy number and threshold cycle ($C_t$), representing the PCR cycle number at which the signal exceeds a given baseline, is seen for all the HPV types tested. Since in the typing assay HPV 18 and 45 use the same probe and therefore are detected together, it is vital that the standard curves for these two HPV types are very similar. Indeed, the curves for HPV 18 and 45 do not only have the same slope but also the same intercept. Similarly, the HPV types 33, 52, 58 and 67 are detected together, using a single probe. Their standard curves have the same slope but differ somewhat with respect to intercept. This may result in a lower precision when viral types within this group are quantified together. Despite the variation seen in intercept seen between HPVs 33, and 58 relative to 52 and 67, the assay is able to quantify the amount with sufficient accuracy. Finally, a significant linear regression was seen between copy number of the human single copy gene and threshold cycle (FIG. 4). The variation seen in the HPV and human DNA quantification systems, expressed as the $C_t$, is shown in Tables 3 and 4. The mean standard deviation (SD) of the $C_t$ values for the HPV assay was 0.89, with the higher values seen for the lower copy numbers (Table 3). The mean standard deviation (SD) of the $C_t$ values for the human gene system was found to be 0.85 (Table 4).

The specificity of the HPV system were tested by determining the ability of the primer and probe combinations in Reaction 1 and Reaction 2 to discriminate against plasmids with different HPV types. The specificity of the reagents in Reaction 1 were tested by analyzing the signal with the HPV types detected in Reaction 2 (i.e. with HPV 33, 35, 39, 52, 58 and 67). No signal was observed with any of these HPV types at $10^4$ initial viral copies (data not shown). Similarly, the specificity of the reagents in Reaction 2 were tested by analyzing the signal with the HPV types detected in Reaction 1 (i.e. for HPV 16, 18, 31,-45). No signal was observed with HPV 16, 18, 31, or 45 at a concentration of $10^4$ initial viral copies (data not shown). The system has not tested for specificity with respect to other HPV types. However, the Reaction 1 and Reaction 2 reagents were designed to be specific for the individual HPV types (using sequence alignments from a large number of HPV types) and Reaction 3 for the nuclear gene (using gene bank and BLAST searches), respectively. Also, an efficient real-time PCR assay is dependent upon the homology of the oligonucleotide probe to the target. As indicated before, about 80-90% of the women diagnosed with cervical tumors are infected with single or multiple HPV of the types detected in this assay. The 10-20% of the remaining tumor biopsies not infected with any of the types in the assay are likely to contain any of a large number of other HPV types, each occurring in very low frequency. Since this assay is not designed to detect these additional HPV types, the rate of false negatives in women diagnosed with severe cervical interstitial neoplasia or invasive cancer is estimated to 10-20%.

Analysis of Mixed Infections

In a previous study of cervical cancer biopsies from Swedish patients about 5% of the samples were infected with several HPV types (Ylitalo et al., 1995). Thus, an important aspect of the present invention is the ability to detect mixed infections between HPV 16 and any of the other more frequent types found to be associated with cervical cancer, such as HPV 18, 31 and 45. We tested the ability of our fluorescent 5' exonuclease assay to correctly detect and quantify HPV titer in samples with multiple infections, by producing synthetic mixtures of known HPV copy numbers using HPV plasmids, in a background of 1 ng of high molecular weight genomic DNA per reaction. First, we tested detection of HPV 18 in a background of HPV 16. For the range $10^2$ to $10^5$ copies of HPV 16, we tested the ability to correctly quantify the amount of HPV 18 over the same range of copy numbers. For example, for $10^5$ copies of HPV 16 we tested the quantification of $10^2$ to $10^5$ copies of HPV 18. The results are shown graphically by relating the log of HPV 18 copy number to the $C_t$. A separate line is given for each copy number of the background HPV 16. The effect of a background HPV type on the correct quantification is seen as a deviation from the linear relationship expected between log HPV copy number and threshold cycle. In the case of quantification of HPV 18 in a background of HPV 16, the assay is able to correctly estimate the HPV 18 copy number in the range $10^4$-$10^5$ copies in a background (mixed infection) of $10^2$ to $10^5$ copies of HPV 16 (FIG. 5*a*). At $10^3$ copies of HPV 18 it can still estimate the copy number although there is a slight deviation from the linear relationships at background levels of HPV 16 between $10^4$ to $10^5$ copies. At $10^2$ copies of HPV 18 it can correctly estimate the copy number across the whole range, except in a background of $10^5$ copies of HPV 16. These results show that the assay is able to quantify the amount of HPV 18 in a background of HPV 16 as long as the HPV 18 occurs in at least 1-10% of the copy number of HPV 16. Similarly, reverse experiments (detection of HPV 16 in a background of HPV 18) demonstrate that an infection of HPV 16 can be detected in a background of HPV 18, as long as the HPV 16 occurs in at least 1-10% of the copy number of HPV 18 (data not shown).

A mixed infection that is likely to occur is HPV 16 together with either HPV 31 or HPV 45. HPV 45 can be correctly quantified at copy numbers between $10^3$-$10^5$, in a background of $10^2$ to $10^5$ HPV 16 copies (FIG. 5*b*). The only exception is at $10^3$ copies of HPV 45 and $10^5$ copies of HPV 16, when the ability to correctly quantify HPV 45 is reduced. Similarly, reverse experiments (detection of HPV 16 in a background of HPV 45), demonstrates that an infection of HPV 16 can be detected in a background of HPV 45 as long as the HPV 16 occurs in at least 1-10% of the copy number of HPV 45 (data not shown). HPV 31 can be quantified in the range $10^2$ to $10^5$ copies, with a background of HPV 16 in the range $10^2$ to $10^4$ copies (FIG. 5*c*). Only in the ratio of $10^2$ copies of HPV 31 to $10^5$ copies of HPV 16 is there no signal from HPV 31. The reverse experiment, i.e. when quantifying HPV 16 in the background of HPV 31, shows that when the HPV 31 copy number is in the range $10^2$ to $10^3$ copies is it possible to quantify HPV 16 copy numbers over the range $10^2$-$10^5$ (data not shown). At higher HPV 31 copy numbers, the quantitative ability with respect to HPV 16 is reduced. Based on the combinations of HPV types tested, that mimic the most common types of mixed infections, the assay is able to correctly quantify the amount of a HPV type as long as it is represents at least 1-10% of the copy number of the major HPV type.

Reproducibility

The reproducibility of the test was studied by repeated measurements of the HPV copy numbers and human DNA in a series of clinical samples.

Intra-Laboratory Reproducibility

A set of clinical samples were analyzed by three different technicians (operators) in the same laboratory and using the same reagent lot. The sample DNA was extracted according to protocol D (see materials and methods). The correspondence between operators with respect to HPV positivity (±) is 98.6% (139/141) and the mean standard deviation in the $C_t$ values between operators is 0.62 units (Table 6). The correspondence in $C_t$ between repeated analyses of a set of clinical samples is shown graphically in FIG. 6. In this experiment a set of cervical swab samples were analyzed using Reaction 1 and 3. A statistically significant linear regression is seen between the results of the two independent experiments ($r^2$=0.99, p>0.0001) (FIG. 6).

Lot-to-Lot Reproducibility

A set of clinical samples was analyzed by a single technician using three different reagents lots. The sample DNA was extracted according to protocol D (see materials and methods). The correspondence between different lots with respect to HPV positivity is 100% (141/141) and the mean standard deviation in the $C_t$ values between the different reagent lots is 0.75 Ct units (Table 7).

Reproducibility Over Time

The set of clinical samples was analyzed by the same technician once every week during a period of four weeks, using the same lot of reagents. The sample DNA was extracted according to protocol D (see materials and methods). The correspondence between the different time-periods with respect to HPV positivity is 98.9% (186/188) and the mean standard deviation in the $C_t$ values between the different time points is 0.19 Ct units (Table 8).

General Variation in Measurements of the Test

The variance in the $C_t$ estimate for amount of HPV or human DNA was calculated using the GLM Procedure in SAS® System. Intra-laboratory variance (Var(error)) amounted to 1.57 $C_t$ units, lot-to-lot variance to 1.45 $C_t$ units, and the variance over-time to 0.76 Ct units. The overall average standard deviation of measurements was 1.1 $C_t$ units. As the measurement range of the system is roughly 20 $C_t$ units (from $C_t$ 15-35), the average variation of the system (1.1 $C_t$) represents about 5% of the range.

Stability

Figure 7A:
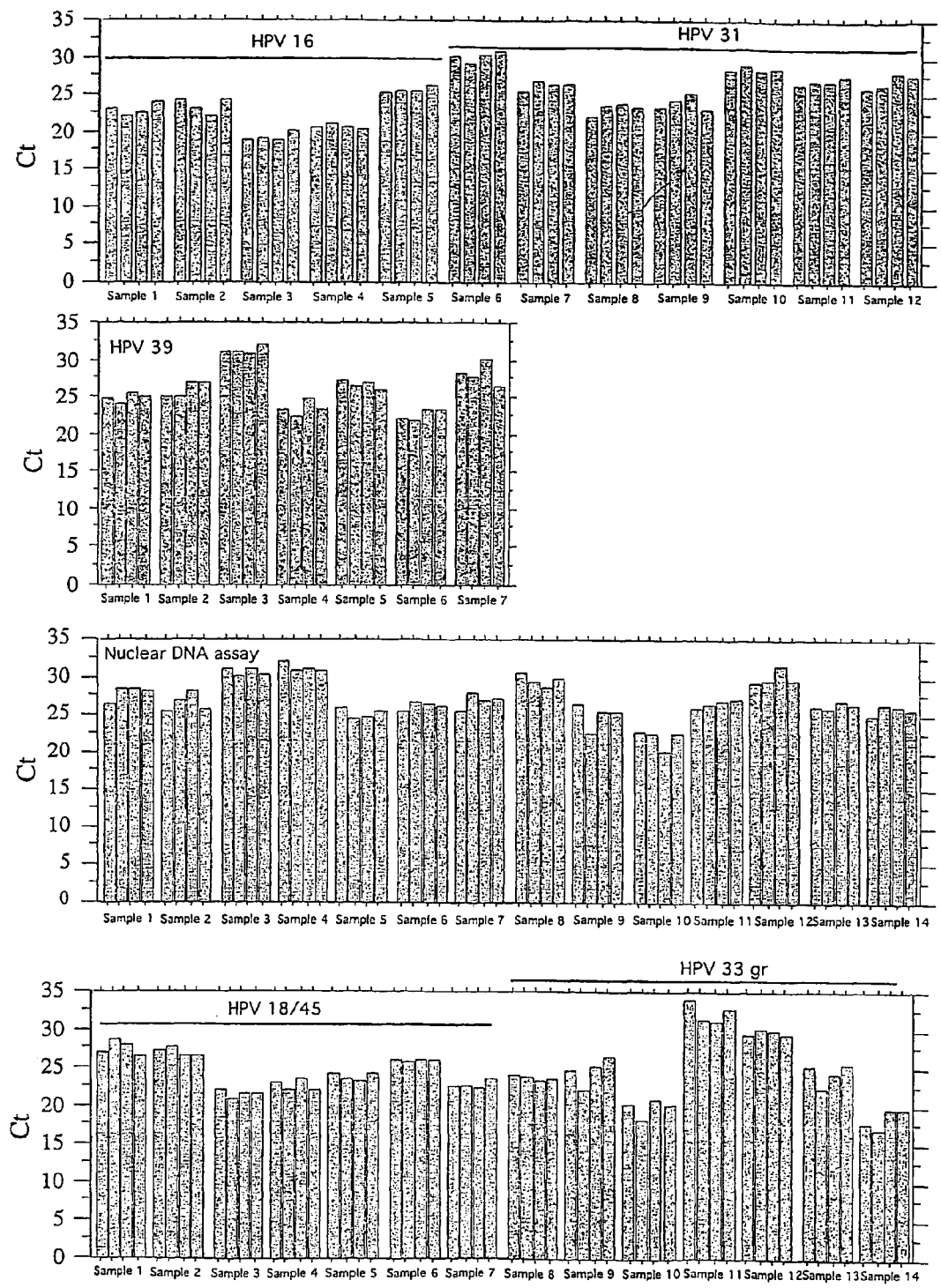

The stability of the assay reagents was examined by studying the amount of HPV and human DNA in a series of clinical samples. The sample DNA was extracted according to protocol D (see materials and methods). The same lot of reagents was employed and the three different storage temperatures tested were −20° C., +4° C. (fridge), and +30° C. (accelerated room temperature stability test). For the −20° C. test, 33 HPV positive samples and 14 samples with human DNA were tested once every week (a test period of 28 days), using the same batch of reagents. No significant change was seen in performance of any of the assays tested over the test period (FIG. 7a). The average SD between time points were for HPV types SD=0.81 $C_t$ (HPV 16, SD=0.60; HPV 31, SD=0.71; HPV 18/45, SD=0.58; the HPV 33 group, SD=1.1; HPV 39, SD=0.91) and for the human DNA SD=0.86 $C_t$. For the +4° C. test, five HPV positive samples and three samples with human DNA were tested seven times over a period of 30 days (day 3, 6, 10, 13, 17, 20, 30), using the same batch of reagents. No significant change was seen in performance of the assay in quantifying the HPV types (HPV 16 and 52) or the human DNA over the 30-day test period (FIG. 7b). The average SD between time points were for the HPV types SD=0.79 $C_t$ (HPV 16, SD=0.88; HPV 52, SD=0.69) and for the human DNA SD=1.4 $C_t$. For the +30° C. test, six HPV positive samples and three samples with human DNA were tested six times over a period of 13 days (day 1, 2, 13, 16, 10, 13), using the same batch of reagents. There is no significant change in performance for the HPV types (HPV 16 and 52) and the human DNA over a period of six days (the initial four samplings) (FIG. 7c). The average SD between the first 4 time points were for the HPV types SD=0.71 $C_t$ (HPV 16, SD=0.84; HPV 52, SD=0.83) and for the human DNA SD=0.77. After six days the reagents fail to function simultaneously for the HPV typing assay and for the human DNA assay.

In summary, the tests at −20° C. and +4° C. show that the variation over the period studied, when performed by the same technician and using reagents from the same lot, is about 1 $C_t$ unit. This is similar to the degree of variation seen in lot-lot comparisons or between operators. Thus, storage at these temperatures over the time periods indicated, does not have any measurable effect on the test reagents. At +30° C. the reagents failed to produce test results after 6 days. Reagents for both HPV and human DNA failed at the same time point.

Sample Preparation

In order to study the performance of the assays on samples of different purity, five different extraction protocols were compared using two different experimental designs. In the first experiment a set of fresh frozen cervical swab samples were each divided in four equal aliquots and subjected to the following extraction protocols; A. Freeze/boiling, B. Wizard kit, C. Digestion, D. Wizard digestion followed by organic extraction, as detailed in the materials and methods. The results of the Taqman assay, using the three first protocols were compared to that of the fourth protocol (used as gold standard). In studying the data for the HPV assay a linear regression analysis based the samples that scored HPV positive using protocol D, shows that protocol B yields the highest correlation to the $C_t$ obtained by D ($r^2$=0.866, p<0.0001) (FIG. 8a). Protocols A ($r^2$=0.974, p<0.0001) and C ($r^2$=0.627, p<0.002) gives lower regression coefficient with the data from that of D (FIG. 8b,c). In comparing the data for the human gene, the differences between the extraction protocols are more pronounced. Again, the results of protocol B show the highest correlation to method D ($r^2$=0.771, p<0.0001) (FIG. 8e). Both protocols A ($r^2$=0.649, p<0.068, non-significant) and C ($r^2$=0.204, p<0.127, non-significant) yield data that does not show a significant correlation with that of D (FIG. 8d,f). Notably, protocols A and C result in a number of samples that score negative for human DNA, preventing a normalization of the amount of HPV. Thus, the results indicate that relative to the organic extraction protocol, which is usually considered unsuited for clinical use, the Wizard kit or the quick protocol with a proteinase K digestion are to be preferred over the very simple freezing/boiling procedure.

Given the results of our comparison between extraction protocols A-D and the widespread use of the freezing/boiling method we performed a second experiment using at set of cervical swab samples collected during routine gynecological health controls, and applied yet another commercial sample preparation method that is frequently being used in diagnostic virology laboratories; the Nuclisens kit. The samples were first extracted using the freeze/boiling method (protocol A) and a Taqman assay performed (Table 8). A number of the samples failed to show the presence of human DNA, although HPV typing proved successful. After application of the Nuclisens kit, the Taqman assay was again performed on these samples and a much higher frequency of samples showed measurable amounts of human DNA (Table 8). Thus, the application of the Nuclisens protocol presumably resulted in the removal of inhibitory agents and a more reliable Taqman assay. The samples used had been previously typed using a separate PCR based assay for scoring the HPV positivity (using the GP5/6 primers). The result of the Taqman assay with respect to HPV positivity was congruent with the results of the previous method (Table 8).

Analysis of Clinical Samples

The assay was tested on a set of over 4723 DNA samples extracted from archival cervical smears taken at routine health controls to examine the performance of the assay (Josefsson et al., 2000). These samples were collected as part of a large case/control study, where cases were diagnosed with cervical cancer in situ. Of the 4723 samples, 4268 (90.6%) gave a signal for the human single copy locus. Among the samples positive for the human gene, the most prevalent HPV type is, as expected HPV 16, with a frequency of almost 22% (FIG. 9). The other HPV types are each found in less than 10% of the samples. Among this set of samples, 185 were infected with at least two HPV types (16/31, n=39; 16/18-45, n=75; 16/33 group, n=40; 18-45/31, n=23; 16/39, n=6; 16/35, n=2) and nine samples were infected with at least three HPV types (16/18-45/31, n=6; 16/31/33 group, n=1; 16/18-45/33 group, n=2). In the mixed infections of HPV 16 and HPV 18/45, the ratio varied from a high of 450 HPV 16 copies per cell in 3 HPV 18 copies per cell to, in the reverse case, 13 HPV 16 copies per cell in 2083 HPV 18 copies per cell. In the mixed infections with HPV 16 and 31, the ratio varied from 1964 HPV 16 copies per cell in 55 HPV 31 copies per cell to, in the reverse case, 9 HPV 16 copies per cell in 697 HPV 31 copies per cell. These results demonstrate the ability of the assay in analyzing mixed infections in clinical samples.

DISCUSSION

The present inventors have developed a quantitative assay for a range of HPV types, suitable for clinical use. A number of methods are available for the detection of HPV in clinical samples. Dichotomous HPV typing (detection of presence or absence of the virus) has limited clinical utility due to the high prevalence of the virus and the fact that most infections clear without an intervention. In the light of the observation that high HPV 16 DNA titer is associated with a significant risk of developing cervical cancer in situ (Josefsson et al., 2000; Ylitalo et al., 2000), analyses of viral titer may have a diagnostic use. Suitable methods for such a titer test must have a wide dynamic range, must be easy to use and permit a range of the highly divergent HPV types associated with the development of cervical dysplasia to be assayed. The present inventors have focused on the real-time PCR since this assay has a number of advantages over other PCR-based methods: (i) requires no further laboratory steps after amplification since data is collection occurs during amplification, (ii) allows for use of multiple detection probes in the same reaction, and (iii) has a wide dynamic range (iv) is a homogeneous assay with a close tube system that limits the potential for contamination of PCR products. The present inventors have extended the usefulness of this method by quantifying three different fluorophores in each reaction tube, limiting the number of parallel reaction that have to be performed. Several other systems for quantification of HPV are based on the use of an internal control (i.e. co-amplification of a human gene) and a comparison between the amount of HPV PCR product and human gene PCR product, using an end point measure of the PCR The present inventors choose to design our system with an external control, to avoid any competition between the amplicons of the HPV and the human gene since such competition may lead to an erroneous estimate of the copy number per cell. Competition between an internal control and a HPV PCR product may result in an underestimate of the HPV copy number for samples with low viral load and an overestimate of HPV copy number in samples with high viral load. A system with an internal control may therefore tend to reduce the range in HPV copy number among samples. The HPV copy number per cell in our samples span over a very wide range. Using a system with an internal control over such a wide range of copy number would most likely limit the resolution of the data substantially.

A separate assay was developed for a single copy nuclear gene, rather than using commercially available assays. Using our human single copy gene assay, the HPV copy numbers can be normalized for the amount of genomic DNA (equivalent to the number of cells included). Given the variation both in the amount of HPV copies between samples and the amount of genomic DNA between samples, such normalization by the number of cells appears necessary to obtain comparable and meaningful HPV titer estimates. Such a measure does not indicate the number of infected cells, or the relative distribution of HPV genomes among cells. However, since the mean number of HPV copies per cell is associated with an increased risk of cancer development, such a measure represents a useful diagnostic indicator independent of the intra- and intercellular distribution of HPV molecules (Josefsson et al., 2000; Ylitalo et al., 2000). An important aspect of any diagnostic technique is the ability to identify false negative samples, resulting either from insufficient amount of starting DNA, or the presence of inhibitors to the PCR. The lack of a signal for the human gene assay either indicates the presence of inhibitors or insufficient amount of DNA in the assay. Indeed, in the comparison of sample extraction protocols we noted that in using one of the faster protocols a number of samples failed to give a signal for the human single copy gene. Most of these samples gave a positive result with the nuclear gene assay when the samples had been further purified.

The assay described in based on standard curves generated from plasmid dilution series. Application of such curves to clinical samples relies on that inhibitors are not present in the sample. Severe inhibition can usually be detected through the nuclear gene assay and the addition of agents such as BSA in the reaction mix reduces the effect of most inhibits. Nevertheless, some sample types may require new standard curves to be generated. For instance, in analyzing formalin-fixed paraffin embedded samples it is necessary to quantify the extent of inhibition using, for instance, the human control assay, before HPV titers can be accurately estimated. A similar problem may occur when analyzing archival Papanicolaou stained smears (Josefsson et al., 1999). At high DNA concentrations, Papanicolaou stained smears show inhibition of the PCR (Josefsson et al., 1999). For quantification of viral copy numbers from tissue samples where BSA does not remove the inhibitory effect, the standard curves used have to be derived from DNA samples handled in an identical way to that of the biological samples.

An important aspect of the assay is the ability to quantify individual HPV types in mixed infections. There are indications that the copy number in infected cervical cells differs not only between different stages of dysplasia (Josefsson et al., 2000; Ylitalo et al., 2000; Swan et al., 1999) but also between HPV types (Swan et al., 1999). Therefore, a diagnostic assay must have the ability to identify and quantitate individual HPV types in a mixed infection. For most combinations of HPV types in our synthetic mixes, the assay showed an ability to detect and quantify an HPV type, as long as it represents at least 1-10% of the amount of the major HPV type. When the ratio between HPV types is less than 1/100, the reduced sensitivity is likely to be due to a competition between the PCR products of different HPV types. For clinical samples infected with several HPV types the ratio vary widely, emphasizing the need for an assay that can provide reliable quantitation over a wide range of ratios.

In summary, the method and kit of the invention as exemplified by the fluorescent 5' exonuclease assay described has a number of characteristics that make it suitable for quantification of HPV viral titers. Other assays exist that have a wide coverage of viral types, but require complex post-PCR analysis, making them unable to compete with the rapidity, convenience and flexibility of the PCR-based fluorecent 5' exonuclease assay.

REFERENCES

Josefsson, A. J., P. K. E. Magnusson, N. Ylitalo, P. Sörensen, P. Qwarforth-Tubbin, P. K. Andersen, M. Melbye, H. O. Adami and U. B. Gyllensten 2000. HPV viral load as a determinant for development of cancer in situ. Lancet 355: 2189-93.

Josefsson, A., K. Livak, and U. Gyllensten. 1999. Detection and real time quantitation of human papillomavirus (HPV) using the fluorescent 5- exonuclease assay (TAQMAN). Journal of Clinical Microbiology, 37,490-496.

Swan D. C., R. A. Tucker, G. Tortolero-Luna, M. F. Mitchell, L. Wideroff, E. R. Unger, R. A. Nisenbaum, W. C. Reeves, J. P. Icenogle 1999. Human papillomavirus (HPV) DNA copy number is dependent on grade of cervical disease and HPV type. J Clin Microbiol 37:1030-4.

Ylitalo, N., A. Josefsson, P. Sörensen, P. Magnusson, P. K. Andersen, J. Pontén, H. O. Adami, U. Gyllensten, and M. Melbye. 2000. Consistent high viral load of human papillomavirus type 16 and risk for cervical carcinoma in situ. Lancet 355:2194-8.

Ylitalo, N., T. Bergstrom, and U. Gyllensten. 1995. Detection of genital human papillomavirus by single-tube nested PCR and type-specific oligonucleotide hybridization. J Clin Microbiol. 33(7):1822-8.

TABLE 1

The PCR primers used in Reaction 1, Reaction 2 and Reaction 3. In denoting the probe, F refers to forward and R to reverse primers. The primers are located in the following reading frames E7, E6, E1, E4 and L1 as given in the primer name and the text.

| | Oligo name | Sequence 5'-3' |
|---|---|---|
| Primers | F16E7 | AGCTCAGAGGAGGAGGATGAA (SEQ ID NO: 1) |
| | R16E7 | GGTTACAATATTGTAATGGGCTC (SEQ ID NO: 2) |
| | F31E6 | ACGATTCCACAACATAGGAGGA (SEQ ID NO: 3) |

TABLE 1-continued

The PCR primers used in Reaction 1, Reaction 2 and Reaction 3. In denoting the probe, F refers to forward and R to reverse primers. The primers are located in the following reading frames E7, E6, E1, E4 and L1 as given in the primer name and the text.

| Oligo name | Sequence 5'-3' |
|---|---|
| R31E6 | TACACTTGGGTTTCAGTACGAGGT (SEQ ID NO: 4) |
| F18E1 | CATTTTGTGAACAGGCAGAGC (SEQ ID NO: 5; SEQ ID NO: 6) |
| R18E1 | ACTTGTGCATCATTGTGGACC (SEQ ID NO: 7) |
| R45E1 | CAACACCTGTGCATCATTCTGA (SEQ ID NO: 8) |
| F35E4 | ACCAAAGCCTGCTCCGTG (SEQ ID NO: 9) |
| R35E4 | AGTCGCACTCGCTTGGTG (SEQ ID NO: 10) |
| F39E7 | CGAGCAATTAGGAGAGTCAGAGGA (SEQ ID NO: 11) |
| R39E7 | CTGTGGTTCATCCCGTCTGG (SEQ ID NO: 12) |
| F3352L1 | CGTCGCAGGCGTAAACGT (SEQ ID NO: 13; SEQ ID NO: 14) |
| R33L1 | ACAGGAGGCAGGTACACTGTGG (SEQ ID NO: 15) |
| F58L1 | TGCGTCGCAGACGTAAACGT (SEQ ID NO: 16) |
| R5258L1 | ACAGGAGGCAGGTACACAGTGG (SEQ ID NO: 17; SEQ ID NO: 18) |
| Hm900 | GCCTGCAGTTTGAAATCAGTG (SEQ ID NO: 19) |
| Hm1018 | CGGGACGGGCTTTAGCTAT (SEQ ID NO: 20) |

TABLE 2

The Taqman hybridisation probes used in Reaction 1
(Pb16E7, Pb31E6 and Pb1845E1), Reaction 2
(Pb335258L1, Pb35E4 and Pb39E7) and
Reaction 3 (PbHm).

|  |  |  | 5' fluorophore | 3' fluorophore |
|---|---|---|---|---|
| Probes | Pb16E7 | CCAGCTGGACAAGCAGAACCGG (SEQ ID NO: 21) | FAM | TAMRA |
|  | Pb31E6 | CTCCAACATGCTATGCAAGGTCC (SEQ ID NO: 22) | TET | TAMRA |
|  | Pb1845E1 | AGAGACAGCACAGGCATTGTTCCATG (SEQ ID NO: 23; SEQ ID NO: 24) | VIC | TAMRA |
|  | Pb335258L1 | AGATGTCCGTGTGGCGGCCTAG (SEQ ID NO: 27; SEQ ID NO: 28; SEQ ID NO: 29) | FAM | TAMRA |
|  | Pb39E7 | AACCCGACCATGCAGTTAATCACCAAC (SEQ ID NO: 26) | TET | TAMRA |
|  | Pb35E4 | CAGAAGACAAATCACAAACGACTTCGAGGG (SEQ ID NO: 25) | VIC | TAMRA |
|  | PbHm | TGGAAGCTAATGGGAAGCCCAGTACC (SEQ ID NO: 30) | VIC | TAMRA |

TABLE 3 a) The variation in Ct for different copy number of HPV types in Reaction 1. Values are based on 12 independent measurements at each copy number.

|  |  | No. of HPV copies | | | | |
|---|---|---|---|---|---|---|
|  |  | 1.0E+06 | 1.0E+05 | 1.0E+04 | 1.0E+03 | 1.0E+02 |
|  |  | | | HPV copies/μl | | |
|  |  | 4.0E+04 | 4.0E+03 | 4.0E+02 | 4.0E+01 | 4.0E+00 |
| HPV16 | Ct | 17.75 | 21.04 | 24.65 | 27.85 | 31.45 |
|  | SD | 0.41 | 0.50 | 0.52 | 0.81 | 0.95 |
| HPV31 | Ct | 18.78 | 22.87 | 26.55 | 29.18 | 33.73 |
|  | SD | 0.77 | 1.64 | 0.60 | 0.84 | 0.71 |
| HPV18 | Ct | 19.04 | 21.43 | 26.02 | 28.82 | 31.95 |
|  | SD | 1.88 | 1.56 | 1.59 | 1.88 | 1.70 |
| HPV45 | Ct | 19.11 | 22.15 | 25.96 | 29.23 | 33.02 |
|  | SD | 0.64 | 0.75 | 0.84 | 0.67 | 0.57 |

TABLE 3 b) The variation in Ct for different copy number of HPV types in Reaction 2. Values are based on 12 independent measurements at each copy number.

|  |  | No. of HPV copies | | | | |
|---|---|---|---|---|---|---|
|  |  | 1.0E+06 | 1.0E+05 | 1.0E+04 | 1.0E+03 | 1.0E+02 |
|  |  | | | HPV copies/μl | | |
|  |  | 4.0E+04 | 4.0E+03 | 4.0E+02 | 4.0E+01 | 4.0E+00 |
| HPV33 | Ct | 19.47 | 22.30 | 25.78 | 29.02 | — |
|  | SD. | 0.54 | 0.55 | 0.87 | 0.64 | — |
| HPV35 | Ct | 20.88 | 24.67 | 27.69 | 30.70 | — |
|  | SD | 0.79 | 0.94 | 1.04 | 1.00 | — |
| HPV39 | Ct | 20.07 | 23.94 | 26.87* | 30.55 | — |
|  | SD | 1.27 | 0.77 | 1.38 | 1.02 | — |
| HPV52 | Ct | 20.48 | 24.10 | 27.90 | 30.84 | — |
|  | SD | 0.58 | 0.60 | 0.88 | 0.53 | — |
| HPV58 | Ct | 20.85 | 24.12 | 27.58 | 30.44 | — |
|  | SD | 0.62 | 0.82 | 0.94 | 0.59 | — |

*n = 11

TABLE 4

The variation in Ct values for different amounts of genomic DNA.
The values are based on 12 measurements at each copy number.

|  |  | DNA-amount (ng) | | | | | | |
|---|---|---|---|---|---|---|---|---|
|  |  | 100.00 | 33.30 | 10.00 | 3.33 | 1.00 | 0.33 | 0.10 |
|  |  |  |  |  | ng/µl |  |  |  |
|  |  | 4.00 | 1.33 | 0.40 | 0.13 | 0.04 | 0.01 | 0.00 |
| Human DNA | Ct | 21.33 | 23.01 | 24.88 | 26.46 | 28.21 | 30.38 | 31.44 |
|  | SD | 0.95 | 0.80 | 0.99 | 0.80 | 1.01 | 0.67 | 0.76 |

TABLE 5

Results of intra-laboratory reproducibility test.

|  | Technician 1 | Technician 2 | Technician 3 |
|---|---|---|---|
| HPV16 | 5/5 | 5/5 | 5/5 |
| HPV31 | 7/7 | 7/7 | 7/7 |
| HPV18/45 | 7/7 | 7/7 | 7/7 |
| HPV33group | 7/7 | 7/7 | 7/7 |
| HPV39 | 6/7 | 6/7 | 7/7 |
| Human DNA | 14/14 | 14/14 | 14/14 |

TABLE 6

Results of the lot-to-lot laboratory reproducibility test.

|  | Lot 1 | Lot 2 | Lot 3 |
|---|---|---|---|
| HPV16 | 5/5 | 5/5 | 5/5 |
| HPV31 | 7/7 | 7/7 | 7/7 |
| HPV18/45 | 7/7 | 7/7 | 7/7 |
| HPV33group | 7/7 | 7/7 | 7/7 |
| HPV39 | 7/7 | 7/7 | 7/7 |
| Human DNA | 14/14 | 14/14 | 14/14 |

TABLE 7

Results of the over-time reproducibility test.

|  | Week | | | |
|---|---|---|---|---|
|  | 1 | 2 | 3 | 4 |
| HPV16 | 5/5 | 5/5 | 5/5 | 5/5 |
| HPV31 | 7/7 | 7/7 | 7/7 | 7/7 |
| HPV18/45 | 7/7 | 7/7 | 7/7 | 7/7 |
| HPV33-group | 6/7 | 7/7 | 7/7 | 7/7 |
| HPV39 | 7/7 | 7/7 | 7/7 | 6/7 |
| Human DNA | 14/14 | 14/14 | 14/14 | 14/14 |

TABLE 8

Comparison of the results using extraction method C and the Nuclisens kit. HPV titers is not normalized with respect to sample amount.

| Sample no | Previous HPV type | Protocol C. (Freezing/Boiling) | | | | Nuclisens extraction protocol | | | |
|---|---|---|---|---|---|---|---|---|---|
|  |  | HPV 16 | HPV 18/45 | HPV33 Group | Human DNA | HPV 16 | HPV 18/45 | HPV33 group | Human DNA |
| 1 | 56* | 0 | 0 | 0 | 0 | 0 | 0 | 0 | 0 |
| 2 | 16, 45, 58 | 0 | 390 | 2.500 | 0 | 270 | 1.400 | 11.000 | 100 |
| 3 | 52 | 0 | 0 | 30 | 30 | 0 | 0 | 3.000 | 150 |
| 4 | 16 | 58 | 0 | 0 | 0 | 140 | 0 | 0 | 1 |
| 5 | 33 | 0 | 0 | 19 | 0 | 0 | 0 | 612 | 12 |
| 6 | 45, 51* | 0 | 0 | 0 | 0 | 0 | 0 | 0 | 40 |
| 7 | 52 | 0 | 0 | 372 | 3.1 | 0 | 0 | 1.365 | 6.5 |
| 8 | 51* | 0 | 0 | 0 | 0 | 0 | 0 | 0 | 6.6 |
| 9 | 56* | 0 | 0 | 0 | 0 | 0 | 0 | 0 | 9.1 |
| 10 | 56* | 0 | 0 | 0 | 0 | 0 | 0 | 0 | 250 |
| 11 | 45 | 0 | 800 | 0 | 0 | 0 | 16.490 | 0 | 97 |
| 12 | 33 | 0 | 0 | 0 | 0 | 0 | 0 | 1.430 | 1.100 |
| 13 | ? | 0 | 0 | 360 | 0 | 0 | 0 | 1.836 | 5.1 |
| 14 | 45 | 0 | 22.5 | 0 | 3 | 0 | 21 | 0 | 14 |
| 15 | 51*, 56* | 0 | 0 | 14 | 0 | 0 | 0 | 2.760 | 690 |

*= HPV types not detected with our assay.

The invention claimed is:

1. A kit for detection and quantification of human papillomavirus, comprising a) the amplification primers SEQ ID NO:1, SEQ ID NO:2, SEQ ID NO:3, SEQ ID NO:4, SEQ ID NO:5/SEQ ID NO:6, SEQ ID NO:7 and SEQ ID NO:8, and the probes SEQ ID NO:21, SEQ ID NO:22 and SEQ ID NO:23/SEQ ID NO:24, for HPV 16, 31, 18, 45; and optionally b) the amplification primers SEQ ID NO:9, SEQ ID NO:10, SEQ ID NO:11, SEQ ID NO:12, SEQ ID NO:13/SEQ ID NO:14, SEQ ID NO:15, SEQ ID NO:16 and SEQ ID NO:17/SEQ ID NO:18 and the probes SEQ ID NO:25, SEQ ID NO:26 and SEQ ID NO:27/SEQ ID NO:28/SEQ ID NO:29 for HPV 33, 35, 39, 52, and 58.

2. A kit according to claim 1, further comprising c) the amplification primers SEQ ID NO:19 and SEQ ID NO:20 and the probe SEQ ID NO:30, for detection and quantification of the amount of a human single copy gene.

3. A kit according to claim 2, wherein the gene is HUMP-BGDA, Homo sapiens hydroxymethylbilane synthase gene, accnr M95623.1.

4. A kit according to claim 1, further comprising d) at least two different fluorophores.

5. A kit according to claim 2, further comprising d) three different fluorophores.

6. A kit according to claim 1 for detection and diagnose of cervical cancer.

7. A kit according to claim 2, further comprising d) at least two different fluorophores.

8. A kit according to claim 3, further comprising d) at least two different fluorophores.

9. A kit according to claim 3 for detection and diagnose of cervical cancer.

10. A kit for detection and quantification of human papillomavirus, comprising a) forward and reverse E7 amplification primers for HPV 16, forward and reverse E1 amplification primers for HPV 18 and 45, and forward and reverse E6 amplification primers for HPV 31, and probes therefore; and optionally b) forward and reverse L1 amplification primers for HPV 33, 52 and 58, forward and reverse E7 amplification primers for HPV 39, and forward and reverse E4 amplification primers for HPV 35, and probes therefore.

11. A kit according to claim 10, further comprising c) forward and reverse amplification primers and a probe therefore, for detection and quantification of the amount of a human single copy gene.

12. A kit according to claim 11, wherein the gene is HUMPBGDA, Homo sapiens hydroxymethylbilane synthase gene, accnr M95623.1.

13. A kit according to claim 10, further comprising d) at least two different fluorophores.

14. A kit according to claim 11, further comprising d) three different fluorophores.

15. A kit according to claim 10 for detection and diagnose of cervical cancer.

* * * * *